(12) United States Patent
Shino

(10) Patent No.: US 8,137,400 B2
(45) Date of Patent: Mar. 20, 2012

(54) TENSILE FORCE-ADJUSTABLE FIXING TOOL FOR FIXING TENDON GRAFT AND LIGAMENT RECONSTRUCTION METHOD

(75) Inventor: Konsei Shino, Suita (JP)

(73) Assignee: Meira Corporation, Nagoya-Shi, Aichi (JP)

( * ) Notice: Subject to any disclaimer, the term of this patent is extended or adjusted under 35 U.S.C. 154(b) by 176 days.

(21) Appl. No.: 12/470,940

(22) Filed: May 22, 2009

(65) Prior Publication Data

US 2010/0298936 A1      Nov. 25, 2010

(30) Foreign Application Priority Data

May 19, 2009    (JP) .................................. 2009-121363

(51) Int. Cl.
*A61F 2/08*         (2006.01)
(52) U.S. Cl. ................... 623/13.13; 623/13.14; 128/898
(58) Field of Classification Search ........................ None
See application file for complete search history.

(56) References Cited

U.S. PATENT DOCUMENTS

| | | | |
|---|---|---|---|
| 5,352,229 A * | 10/1994 | Goble et al. ................... 606/75 |
| 6,117,139 A | 9/2000 | Shino | |
| 6,325,804 B1 * | 12/2001 | Wenstrom et al. .......... 623/13.12 |
| 6,497,726 B1 * | 12/2002 | Carter et al. ................ 623/13.17 |
| 7,766,964 B2 * | 8/2010 | Stone et al. ................. 623/13.13 |
| 2003/0009218 A1 * | 1/2003 | Boucher et al. ............. 623/13.14 |
| 2004/0034353 A1 * | 2/2004 | Michelson ....................... 606/61 |
| 2007/0032870 A1 | 2/2007 | Sklar et al. | |
| 2007/0233151 A1 * | 10/2007 | Chudik ........................... 606/96 |

FOREIGN PATENT DOCUMENTS

EP           1297799 A2      4/2003

* cited by examiner

*Primary Examiner* — Thomas J Sweet
*Assistant Examiner* — Rebecca Straszheim
(74) *Attorney, Agent, or Firm* — Buchanan Ingersoll & Rooney PC

(57) ABSTRACT

A fixing tool used in a ligament reconstruction operation includes a fixing member having a main body part provided with a through-hole and two spike parts which can be stricken into the bone and a fixing screw. The fixing screw includes a shaft part having a self-tap portion and a male screw portion, a head part, and a lumen. The fixing screw can be screwed into the bone plug in a state where a guide pin pierced into the bone plug penetrates the lumen of the fixing screw and a pulling member mounted to the bone plug and extended from the bone tunnel is being pulled. The fixing screw can adjust a tensile force of the tendon graft by adjusting the amount of screwing of the fixing screw into the bone plug after the head part of the fixing screw contacts the fixing member.

6 Claims, 33 Drawing Sheets

TENSILE FORCE-ADJUSTABLE FIXING TOOL FOR FIXING TENDON GRAFT AND LIGAMENT RECONSTRUCTION METHOD

BACKGROUND OF THE INVENTION

The present invention relates to a fixing tool used in a ligament reconstruction operation to fix a tendon graft having a bone plug can be inserted into a bone tunnel formed at a bone and a ligament reconstruction method to be carried out by using the tendon graft having a bone plug.

In a ligament reconstruction operation (for example, anterior cruciate ligament reconstruction operation) currently performed, a first tunnel (bone tunnel at tibial side) is formed at the tibia, whereas a second tunnel (bone tunnel at femur) is formed at the femur. In a normal ligament reconstruction operation, a tendon graft for reconstructive use (for example, hamstring muscles folded four to six times) is not long enough to pass the tendon graft through the bone tunnel consisting of the first tunnel, inside the joint, and the second tunnel. Therefore an artificial ligament or a sewing thread is placed at both ends of the tendon graft for reconstructive use to fix the ligament to a portion in the neighborhood of an upper opening of a bone tunnel at the femur side and thereafter finally fix the ligament to a front opening of the bone tunnel at the tibial side.

A method of using an autogenous/allogeneic bone plug-attached patellar tendon as the ligament graft for reconstructive use is widely carried out. The following fixing methods and appliances using the bone plug-attached patellar tendon are known: the screw for fixing a tendon graft to be transplanted inside a bone tunnel is disclosed in U.S. Patent Publication No. 2007/0032870. The tendon graft fixing screw has the screw thread in the range from the distal end thereof to the proximal end thereof and the flat surface at the proximal side thereof. The expandable fixing apparatus disclosed in European Patent Publication No. 1297799 is inserted between the tibia-side bone tunnel and the tibia-side bone plug of the ligament for reconstructive use to fix the tendon graft. The tendon graft-fixing appliance, disclosed in U.S. Pat. No. 6,117,139, having two spikes and the ligaturing hole is stricken into a portion in the neighborhood of the tibia-side bone tunnel to bind the sewing thread sewed to the tibia-side bone plug of the tendon for reconstructive use to the ligaturing hole. In another known tendon graft fixing appliance, the screw is inserted into a portion in the neighborhood of the tibia-side bone tunnel to bind the sewing thread sewed to the tibia-side bone plug of the tendon for reconstructive use to the head part thereof. In this manner, the ligament for reconstructive use is fixed.

But it is difficult for the above-described fixing appliances and fixing methods to fix the tendon graft for reconstructive use at a tensile force intended by an operator.

It is an object of the present invention to solve the above-described problem and provide a tensile force-adjustable fixing tool for fixing a tendon graft having a bone plug to be transplanted at a tensile force intended by an operator and a ligament reconstruction method to be carried out by using the tendon graft having the bone plug.

SUMMARY OF THE INVENTION

The above-described object is achieved by a fixing tool.

A fixing tool used in a ligament reconstruction operation to fix a tendon graft having a bone plug can be inserted into a bone tunnel formed at a bone; wherein said fixing tool comprises a fixing member and a fixing screw, wherein said fixing member includes a main body part provided with a through-hole formed at a central portion thereof and two spike parts which extend almost parallelly from both side edges of said main body part with said spike parts spaced at a predetermined interval longer than a diameter of said bone tunnel and can be stricken into said bone; said fixing screw includes a shaft part having a self-tap portion and a male screw portion both of which can be penetrated through said through-hole of said fixing member and screwed into said bone plug, a head part which is disposed at a proximal end of said shaft part and can be brought into contact with said main body part along a peripheral edge of said through-hole of said fixing member, and a lumen which is extended from a proximal end of said head part to a distal end of said shaft part and through which a guide pin pierced into said bone plug can be penetrated; and in a state where said main body part of said fixing member is stricken into a portion in a neighborhood of said bone tunnel with said main body part crossing an opening of said bone tunnel, said through-hole of said fixing member is located at a position in a neighborhood of a center of said opening of said bone tunnel, and a pulling member mounted on said tendon graft is extendable from a gap between said main body part of said fixing member and said opening of said bone tunnel, said fixing screw can be screwed into said bone plug in a state where a guide pin pierced into said bone plug is penetrated through said lumen of said fixing screw and said pulling member extended from said gap is being pulled; and said fixing member can be adjusted a tensile force of said tendon graft by adjusting an amount of screwing of said fixing screw into said bone plug after said head part of said fixing screw contacts to said fixing member.

The above-described object is achieved by a fixing appliance.

A fixing appliance used in a ligament reconstruction operation, comprising a fixing tool for fixing a tendon graft having a bone plug can be inserted in a bone tunnel formed at a bone and a striking tool for striking said fixing tool into said bone, wherein said fixing tool comprises a fixing member and a fixing screw, wherein said fixing member includes a main body part provided with a through-hole formed at a central portion thereof and two spike parts which extend almost parallelly from both side edges of said main body part with said spike parts spaced at a predetermined interval longer than a diameter of said bone tunnel and can be stricken into said bone; said fixing screw includes a shaft part having a self-tap portion and a male screw portion both of which can be penetrated through said through-hole of said fixing member and screwed into said bone plug, a head part which is disposed at a proximal end of said shaft part and can be brought into contact with said main body part along a peripheral edge of said through-hole of said fixing member, and a lumen which is extended from a proximal end of said head part to a distal end of said shaft part and through which a guide pin pierced into said bone plug can be penetrated; and in a state where said main body part of said fixing member is stricken into a portion in a neighborhood of said bone tunnel with said main body part crossing an opening of said bone tunnel, said through-hole of said fixing member is located at a position in a neighborhood of a center of said opening of said bone tunnel, and a pulling member mounted on said tendon graft is extendable from a gap between said main body part of said fixing member and said opening of said bone tunnel, said fixing screw can be screwed into said bone plug in a state where a guide pin pierced into said bone plug is penetrated through said lumen of said fixing screw and said pulling member extended from said gap is being pulled; and said fixing member can be adjusted a tensile force of said tendon graft by adjusting an amount of screwing of said fixing screw into said bone plug after said head part of said fixing screw contacts to said fixing member, and said striking tool has a shaft part extended in a predetermined length; a fixing member-gripping part, provided at a distal end of said shaft part, for removably gripping said main body part of said fixing member; and a proximal end portion for being hammered which is provided at a proximal end of said shaft part.

The above-described object is achieved by an anterior cruciate ligament reconstruction method.

An anterior cruciate ligament reconstruction method to be carried out by using a patellar tendon having a bone plug at both ends thereof as a tendon graft to be transplanted, comprising the steps of: preparing said tendon graft having said bone plug at both ends thereof; mounting a pulling member on each of said bone plugs of said tendon graft respectively; forming a femur-side bone tunnel and a tibia-side bone tunnel on a portion to be reconstructed; disposing said tendon graft at said portion to be reconstructed in such a way that one of said bone plugs is positioned inside said tibia-side bone tunnel and the other of said bone plugs is positioned inside said femur-side bone tunnel; fixing other side of said tendon graft to said femur; striking a fixing member having a main body part provided with a through-hole formed at a central portion thereof and two spike parts which extend almost parallelly from both side edges of said main body part with said spike parts spaced at a predetermined interval longer than a diameter of said tibia-side bone tunnel to a portion in a neighborhood of said tibia-side bone tunnel in such a way that said main body part crosses an opening of said bone tunnel; piercing a guide pin to said one of bone plugs through said through-hole of said fixing member; disposing a fixing screw including a shaft part having a self-tap portion and a male screw portion both of which can be penetrated through said through-hole of said fixing member and are screwed into said one of bone plugs, a head part which is disposed at a proximal end of said shaft part and can be brought into contact with said main body part on a peripheral edge of said through-hole of said fixing member, and a lumen which is extended from a proximal end of said head part to a distal end of said shaft part and through which said guide pin can be penetrated in such a way that said guide pin penetrates through said lumen of said fixing screw and that said fixing screw is advanced along said guide pin to penetrate said guide pin through said through-hole of said fixing member and bring a distal end of said fixing screw into contact with said one of bone plugs; screwing said fixing screw into said one of bone plugs; pulling said pulling member mounted on said one of bone plugs and extended from a gap between said main body part of said fixing member and an opening of said tibia-side bone tunnel and measuring a pulling-caused tensile force applied to said pulling member; progressing screwing of said fixing screw into said one of bone plugs and bringing said head part of said fixing screw into contact with said fixing member; and adjusting said tensile force applied to said pulling member by progressing screwing of said fixing screw into said one of bone plugs till said tensile force applied to said pulling member being measured attains a predetermined value after said head part of said fixing screw contacts said fixing member.

DETAILED DESCRIPTION OF THE PREFERRED EMBODIMENTS

Figure 1:
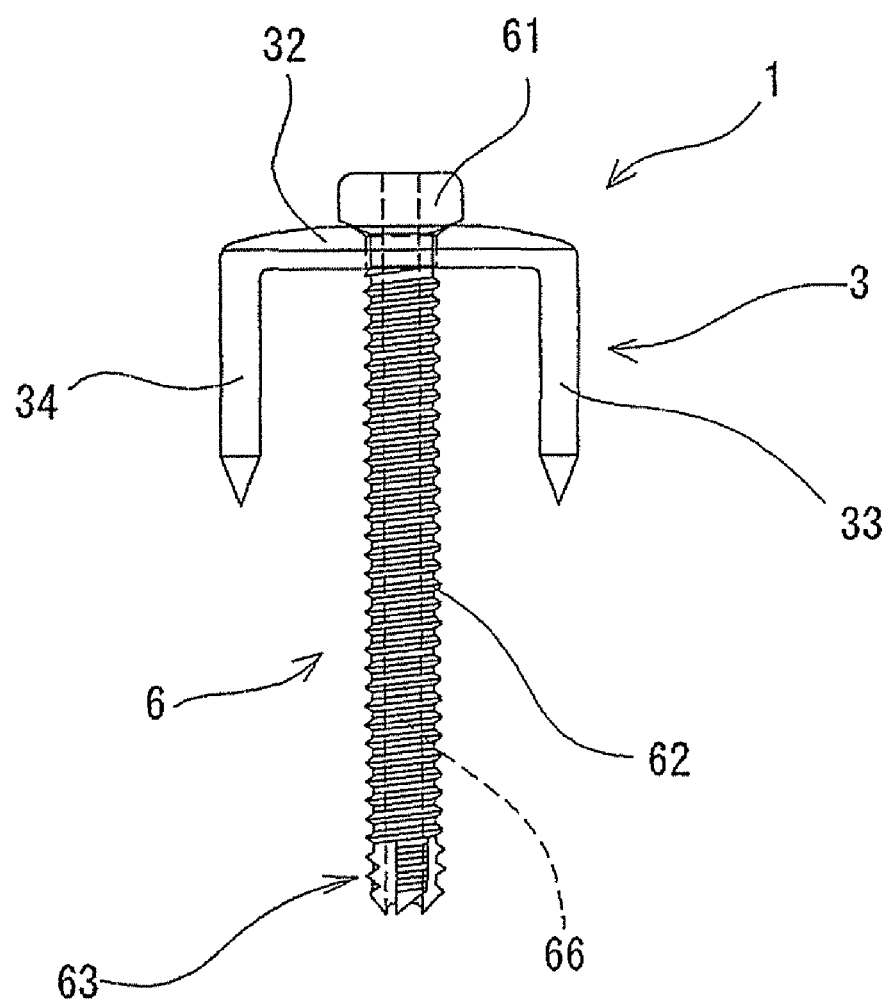
FIG. 1 is a front view of a fixing tool, of an embodiment of the present invention, for fixing a tendon graft.
Figure 2:
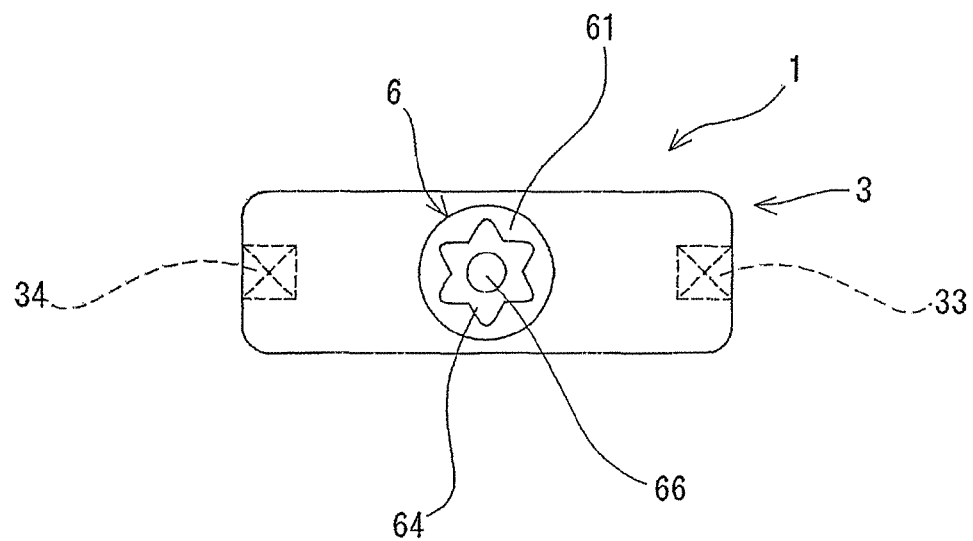
FIG. 2 is an enlarged plan view of the fixing tool for fixing the tendon graft shown in FIG. 1.
Figure 3:
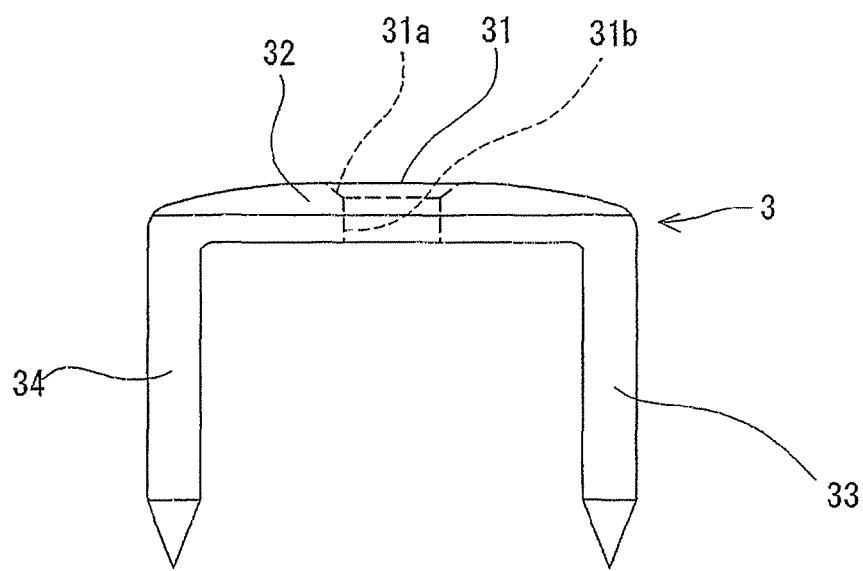
FIG. 3 is an enlarged front view of a fixing member to be used for the fixing tool shown in FIG. 1.
Figure 4:
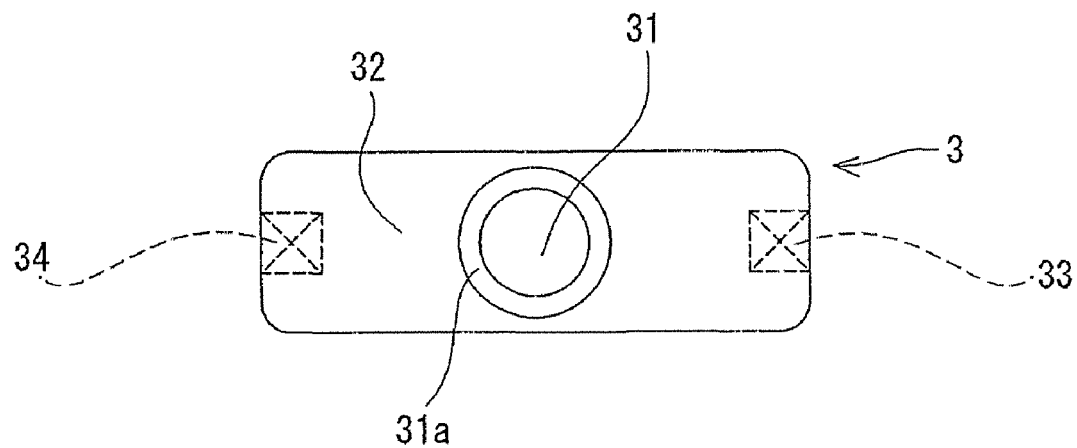
FIG. 4 is a plan view of the fixing member shown in FIG. 3.
Figure 5:
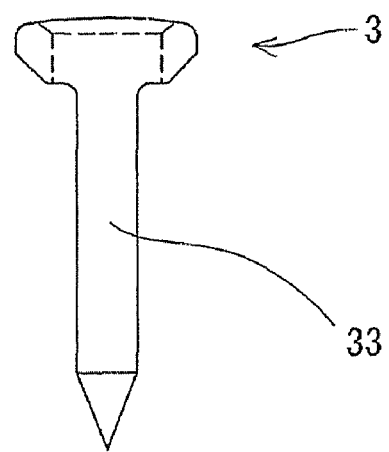
FIG. 5 is a right-hand side view of the fixing member shown in FIG. 3.

Embodiments of a fixing tool of the present invention for fixing a tendon graft having a bone plug (in other words, bone piece) are described below.

The fixing tool 1 of the present invention is used in a ligament reconstruction operation to fix a tendon graft 2 having a bone plug can be inserted into a bone tunnel formed at a bone. In other words, the fixing tool 1 of the present invention is used to fix a bone plug attached to at least one end of a tendon graft 2 inside a bone tunnel formed at a portion where the tendon graft 2 is to be transplanted and other end of the tendon graft 2 is fixed. The fixing tool 1 of the present invention is a tensile force-adjustable fixing tool.

The fixing tool 1 comprises a fixing member 3 and a fixing screw 6.

The fixing member 3 has a main body part 32 provided with a through-hole 31 formed at a central portion thereof and two spike parts 33, 34 which extend almost parallel from both side edges of the main body part 32 with the spike parts 33, 34 spaced at a predetermined interval longer than the diameter of a formed bone tunnel and can be stricken into a bone.

The fixing screw 6 has a shaft part 65 having a self-tap portion 63 and a male screw portion 62 both of which can be penetrated though the through-hole 31 of the fixing member 3 and screwed into a bone plug (one-end side bone plug 21), a head part 61 which is disposed at a proximal end of the shaft part 65 and can be brought into contact with the main body part 32 along a peripheral edge of the through-hole 31 of the fixing member 3, and a lumen 66 which is extended from a proximal end of the head part 61 to a distal end of the shaft part 65 and through which a guide pin 85 pierced into the bone plug can be penetrated.

In the fixing tool 1 for fixing the tendon graft to be transplanted, in a state where the main body part 32 of the fixing member 3 is stricken into a portion in the neighborhood of the bone tunnel (bone tunnel 8 at the tibial side) with the main body part 32 crossing an opening (open portion 81) of the bone tunnel, the through-hole 31 is located at a position in the neighborhood of the center of the opening 81 of the bone tunnel 8, and a pulling member 22 mounted on the tendon graft 2 to be transplanted is extendable from the gap between the main body part 32 and the opening 81 of the bone tunnel 8.

The fixing screw 6 can be screwed into the bone plug (one-end side bone plug 21) in a state where a guide pin 85 pierced into the bone plug 21 is penetrated through the lumen 66 of the fixing screw 6 and the pulling member 22 extended from the gap of the bone tunnel 8 is being pulled. The fixing screw 6 can be adjusted a tensile force of the tendon graft 2 by adjusting an amount of screwing of the fixing screw 6 into the bone plug 21 after the head part 61 of the fixing screw contacts to the fixing member 3.

The tensile force-adjustable fixing tool 1 of this embodiment for fixing the tendon graft is used for performing a ligament reconstruction operation. In an anterior cruciate ligament reconstruction operation, it is preferable to use the fixing tool 1 in fixing the bone plug (one-end side bone plug 21) of the tendon graft inside the tibia-side bone tunnel 8. In addition, it is possible to use the fixing tool of the present invention in carrying out a ligament reconstruction operation (for example, posterior cruciate ligament reconstruction operation) other than the anterior cruciate ligament reconstruction operation and fix the bone plug of the tendon graft to portions other than the tibia-side bone tunnel 8 (for example, femur-side bone tunnel 9).

As shown in FIGS. 1 through 5, the fixing member 3 which is used for the fixing tool 1 of the present invention for fixing the tendon graft has the main body part 32, the through-hole 31 formed at the central portion of the main body part 32, and the two spike parts 33, 34 extended from the main body part 32.

The main body part 32 is formed in the shape of approximately a flat plate. The main body part 32 may be formed in the shape of a bent plate or a curved plate. The two spike parts 33, 34 extend almost parallelly from both side edges of the main body part 32 with the spike parts 33, 34 spaced at the predetermined interval longer than the diameter of the formed bone tunnel. It is preferable that the interval between the spike parts 33 and 34 is longer than the diameter of the open portion 81 of the tibia-side bone tunnel 8 to such an extent that the fixing member 3 can be stricken into the tibia 10 without breaking the periphery of the open portion 81 of the tibia-side bone tunnel 8. In the fixing member 3 of this embodiment, the spike parts 33, 34 extend almost parallelly from both side edges of the main body part 32 and almost orthogonally to the main body part 32. It is preferable to set the length of the spike parts 33, 34 to 8 to 18 mm and especially preferable to set the length thereof to 11 to 16 mm. It is preferable to set the width of the spike parts 33, 34 to 1.7 to 2.5 mm and especially preferable to set the length thereof to 1.9 to 2.2 mm. Each of the spike parts 33, 34 has a pointed end portion which is pierced into the tibia 10 at a distal end thereof. As the form of the pointed end portion of the spike parts 33, 34, conic, three-sided pyramidal, and four-sided pyramidal configurations are listed. As the configuration of portions of the spike parts 33, 34 other than the pointed end portion, a column, a triangular prism, and a square pillar are preferable. As the configuration of the spike parts 33, 34 of this embodiment, the pointed end portion has the shape of a four-sided pyramid, whereas portions thereof other than the pointed end portion has the shape of a square pillar. The configuration of the spike parts 33, 34 is not limited to the above-described one. The spike parts 33, 34 may be so configured that the inner side thereof and that of the outer side thereof are different from each other. For example, as with a fixing member 3a shown in FIGS. 8 through 10, it is preferable that opposed inner sides of spike parts 93, 94 do not substantially have a corner but have a curved surface. The inner side of each of the spike parts 93, 94 does not have a corner but is columnar, whereas the outer side of each of the spike parts 93, 94 has a corner and thus has the shape of a square pillar. Thereby it is possible to decrease the extent of an impact to be imparted to the wall of the tibia-side bone tunnel when the spike parts are stricken into the tibia 10 (or pilot holes 56, 57 described later).

At the center of the main body part 32, there is formed the through-hole 31 through which the shaft part 65 of the fixing screw 6 described later is penetrated. In the state where the main body part 32 of the fixing member 3 is stricken into a portion in the neighborhood of the bone tunnel (the bone tunnel 8 at the tibia side) with the main body part 32 crossing the opening (the open portion 81) of the bone tunnel, the through-hole 31 is located at a position in the neighborhood of the center of the opening (the open portion 81) of the bone tunnel 8 (the bone tunnel 8 at the tibia side). The through-hole 31 is circular, elliptic, and the like and is preferably circular. In this embodiment, the through-hole 31 is circular. It is preferable that the diameter of the through-hole 31 is so set that the shaft part 65 of the fixing screw 6 described later can be inserted therethrough and that the head part 61 of the fixing screw 6 contacts the periphery of the through-hole 31. The through-hole 31 has an open portion 31a whose diameter taperingly decreases toward the side at which the spike part is formed and an opening 31b continuous with the open portion 31a and not having a thread groove. The inner diameter of the opening 31b is set larger than the outer diameter of the shaft part 65 of the fixing screw 6 described later. The open portion 31a whose diameter taperingly decreases is capable of contacting a tapered portion 61a whose diameter taperingly decreases toward the distal end, of the head part 61 of the fixing screw 6, which is disposed at a lower peripheral portion of the head part 61 or accommodating the tapered portion 61a.

Figure 8:
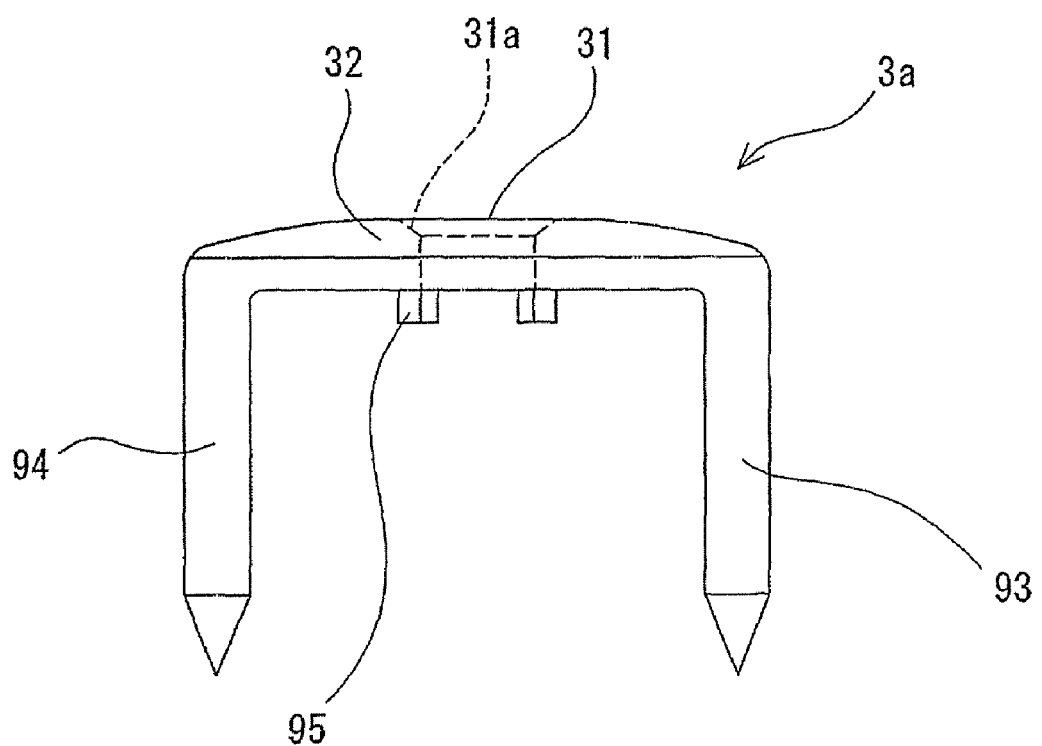
FIG. 8 is a front view of a fixing member to be used for the tensile force-adjustable fixing tool of another embodiment of the present invention.
Figure 9:
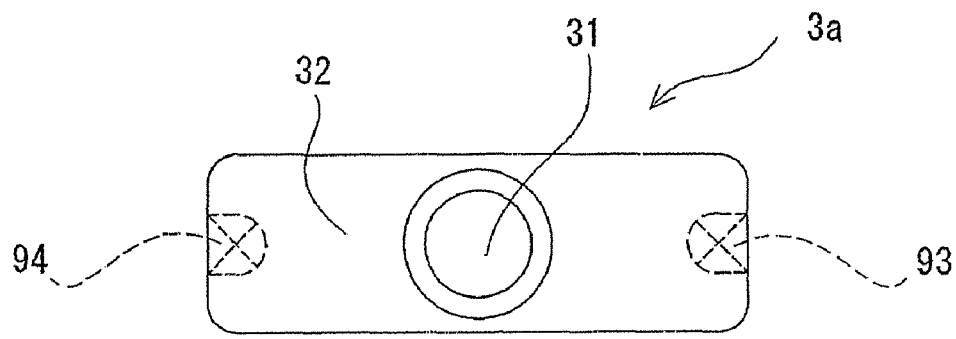
FIG. 9 is a plan view of the fixing member shown in FIG. 8.
Figure 10:
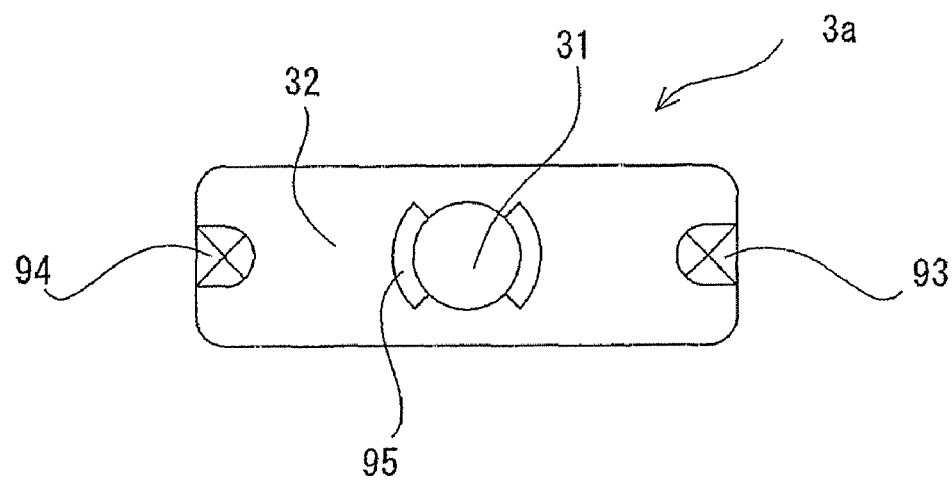
FIG. 10 is a bottom view of the fixing member shown in FIG. 8.

As with a fixing member 3a shown in FIGS. 8 through 10, the main body part 32 may have a bone tunnel-protecting projected portion 95 which is formed on the periphery of the through-hole 31 at the side thereof where the spike part is formed and enterable into the bone tunnel (the bone tunnel 8 at the tibia side), with the bone tunnel-protecting projected portion 95 sliding on an inner wall surface of the bone tunnel or approaching the inner wall surface thereof. The bone tunnel-protecting projected portion 95 for protecting the bone tunnel prevents the breakage of the bone tunnel 8 at the tibia side, the deflection of the fixing member, and the occurrence of an unexpected movement thereof.

As materials for forming the fixing member 3, stainless steel (more specifically, SUS304, SUS316 of JISG4303) and pure titanium (more specifically, JIST7401-1), titanium alloy (more specifically, Ti-6Al-4V, ASTMF-136 Ti-6Al-4V ELI of JIST7401-2) are preferable.

Figure 26:
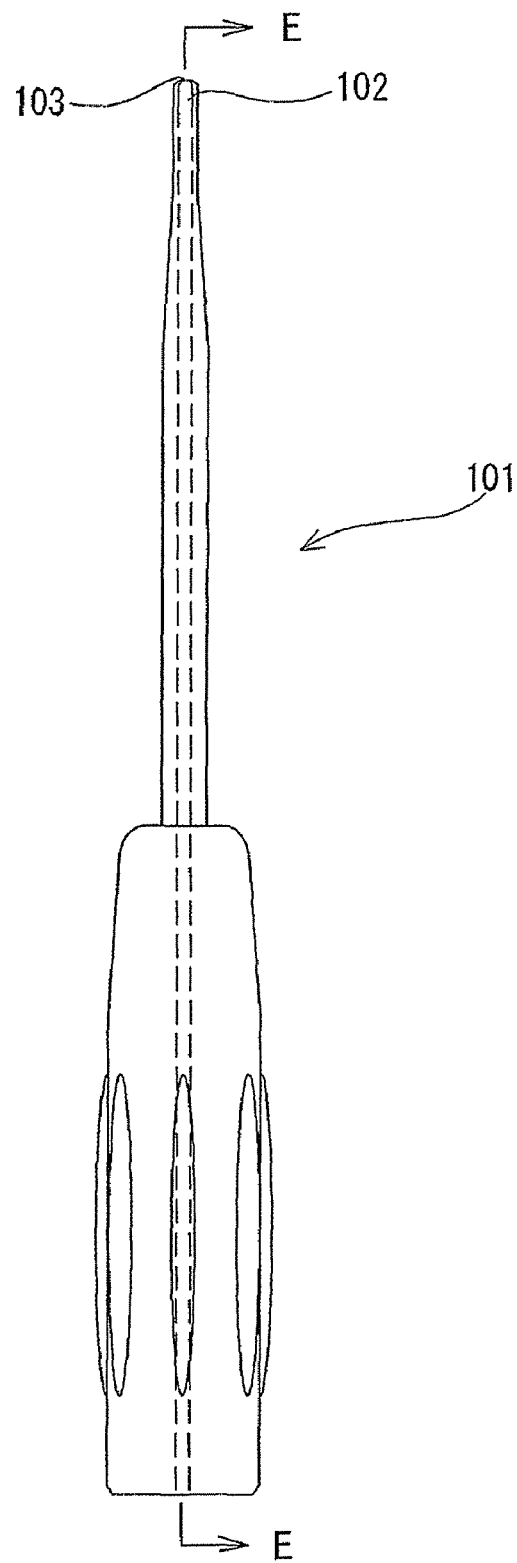
FIG. 26 is a front view of a screwing appliance utilized in the present invention.
Figure 27:
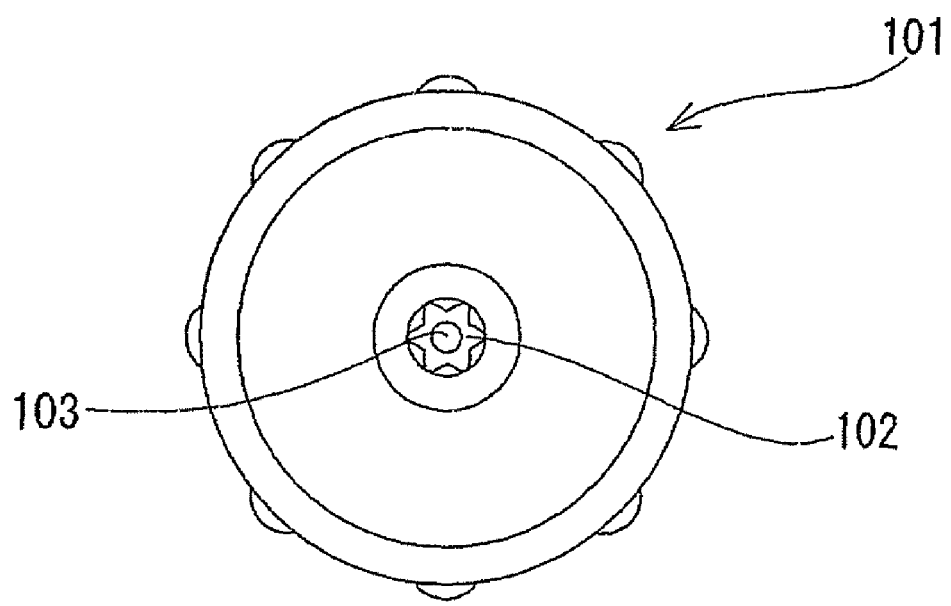
FIG. 27 is an enlarged plan view of the screwing appliance shown in FIG. 26.
Figure 28:
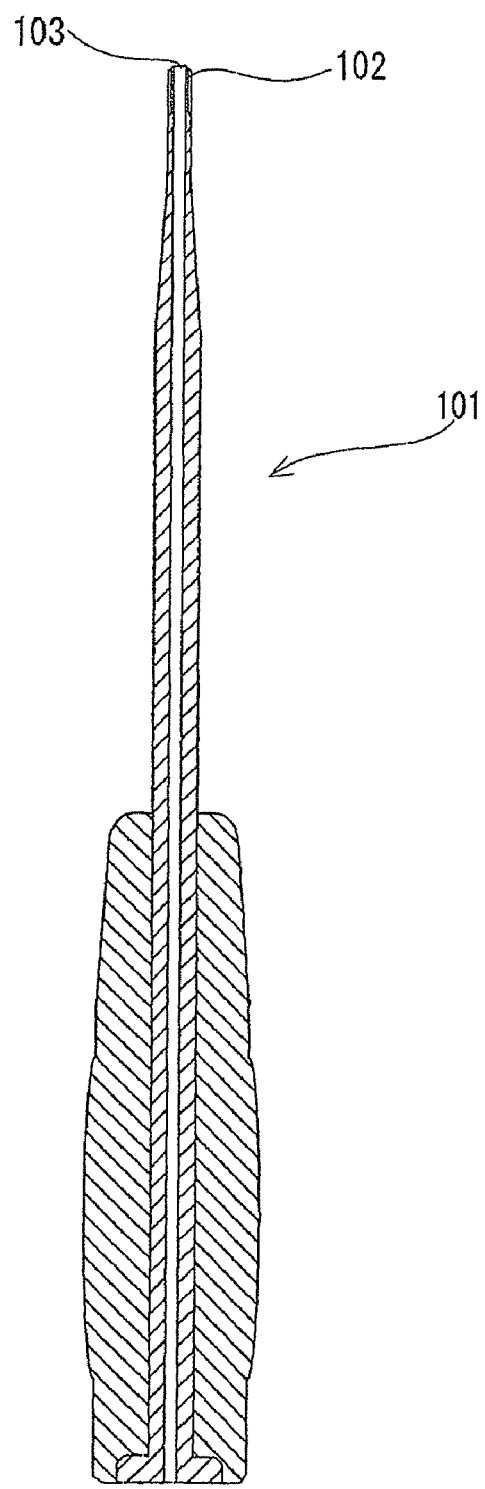
FIG. 28 is a sectional view taken along a line E-E of FIG. 26.

As shown in FIGS. 1, 2, 6, and 7, the fixing screw 6 for use in the fixing tool 1 of this embodiment has the shaft part 65 having the self-tap portion 63 and the male screw portion 62, both of which are penetrable through the through-hole 31 of the fixing member 3 and are screwed into the bone plug of the tendon graft; the head part 61 which is disposed at the proximal end of the shaft part 65 and can be brought into contact with the main body part 32 on the peripheral edge of the through-hole 31 of the fixing member 3; and the lumen 66 which is extended from the proximal end of the head part 61 to the distal end of the shaft part 65 and through which the guide pin 85 pierced into the bone plug is penetrable. The head part 61 has an engaging groove 64 having a configuration corresponding to that of a distal end 102 of a screwing appliance 101 (more specifically, hollow driver) shown in FIGS. 26 through 28. The engaging groove 64 is capable of engaging the distal end 102.

Figure 6:
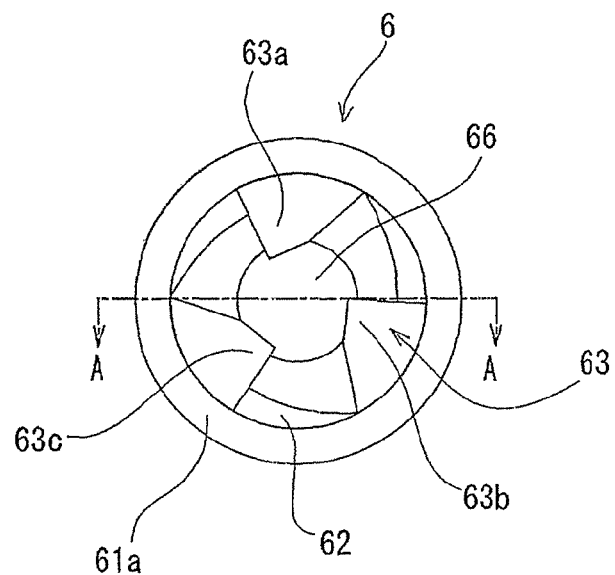
FIG. 6 is an enlarged bottom view of a fixing screw to be used for the fixing tool shown in FIG. 1.

The shaft part 65 has the male screw portion 62 on its side surface and the self-tap portion 63 at its distal end. As shown in FIG. 6, the self-tap portion 63 is constructed of three blades 63a, 63b, and 63c formed by cutting out the distal surface of the shaft part 65 at regular intervals in the circumferential direction thereof. The self-tap portion 63 cuts the one-end side bone plug 21 of the tendon graft 2 and enters thereinto during the rotation of the fixing screw 6, thus forming a female screw portion which engages the male screw portion 62 on the one-end side bone plug 21. The length of the shaft part 65 is favorably 10 to 30 mm and more favorably 15 to 20 mm. It is preferable that the diameter of the shaft part 65 is set smaller than that of the through-hole 31 of the fixing member 3 to such an extent that the shaft part 65 is capable of penetrating through the through-hole 31. Thereby the shaft part 65 is penetrable through the through-hole 31. The diameter of the shaft part 65 is favorably 2 to 6 mm and more favorably 3 to 5 mm.

The head part 61 of the fixing screw 6 is disposed at the proximal end of the shaft part 65 and has the engaging groove 64, formed on its surface at its proximal side, which engages the screwing appliance 101 which is described later. The diameter of the head part 61 is set larger than that of the through-hole 31, of the fixing member 3. Thereby as shown in FIG. 1, the head part 61 of the fixing screw 6 is capable of contacting the main body part 32 of the fixing member 3 on the peripheral edge of the through-hole 31 of the fixing member 3. That is, the main body part 32 of the fixing member 3 is capable of preventing the fixing screw 6 from moving to the distal side thereof.

Figure 7:
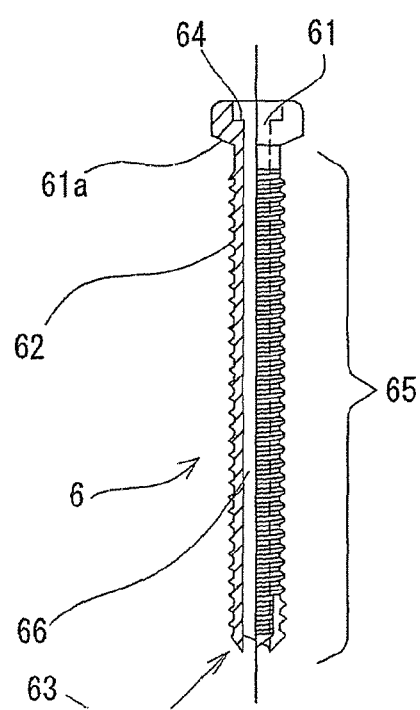
FIG. 7 is a partly broken-away sectional miniature view of the fixing screw taken along a line A-A shown in FIG. 6.

As shown in FIG. 7, the head part 61 of the fixing screw 6 has a tapered portion 61a formed at a lower peripheral edge (see FIG. 6) thereof. The diameter of the tapered portion 61a decreases to the distal end thereof. The tapered portion 61a, formed on the lower peripheral edge of the head part 61 of the fixing screw 6, which decreases to the distal end thereof in its diameter is capable of contacting the open portion 31a whose diameter taperingly decreases to the side of the fixing member 3 at which the spike part is formed or penetrating into the open portion 31a. The outer diameter of the shaft part 65 of the fixing screw 6 is set smaller than the inner diameter of the opening 31b of the through-hole 31 of the fixing member 3.

The fixing screw 6 is hollow. That is, the fixing screw 6 has the lumen 66 penetrating through the fixing screw 6 from the proximal end of the head part 61 thereof to the distal end of the shaft part 65 thereof. More specifically, as shown in FIG. 7, the fixing screw 6 has the lumen 66 penetrating therethrough from the engaging groove 64 of the head part 61 to the distal end of the self-tap portion 63 formed at the distal end of the shaft part 65. The lumen 66 allows the guide pin 85 to be inserted into (through) the fixing screw 6. Thereby with the guide pin 85 inserted into the lumen 66 (in other words, with the guide pin 85 penetrated through the lumen 66) of the fixing screw 6 after the guide pin 85 is pierced into the bone plug (one-end side bone plug 21), the fixing screw 6 is advanced. Thereby the fixing screw 6 can be penetrated through the through-hole 31 of the fixing member 3 and screwed into the bone plug (one-end side bone plug 21) with the distal end (self-tap portion 63) of the shaft part 65 in contact with the bone plug (one-end side bone plug 21). It is preferable that the lumen 66 of the fixing screw 6 has a configuration not imparting a torque to the guide pin 85 during the rotation of the fixing screw 6. More specifically, it is preferable that the lumen 66 of the fixing screw 6 is circular or elliptic in its section orthogonal to its axial direction. It is especially preferable that the lumen 66 of the fixing screw 6 is perfectly circular in its section orthogonal to its axial direction.

In the state where the main body part 32 of the fixing member 3 has been stricken into a portion in the neighborhood of the bone tunnel (tibia-side bone tunnel 8) with the main body part 32 crossing the opening (open portion 81) of the bone tunnel, the shaft part 65 of the fixing screw 6 penetrates through the through-hole 31 of the fixing member 3 and the open portion 81 (front opening) of the tibia-side bone tunnel 8 and screws into the one-end side bone plug 21 inside the tibia-side bone tunnel 8. Owing to the contact between the head part 61 of the fixing screw 6 and the main body part 32 of the fixing member 3, the bone plug-attached tendon graft 2 is prevented from moving to the other-end side bone plug (or to fixing appliance at femur side). Thereby the one-end side bone plug 21 is fixed inside the tibia-side bone tunnel 8.

The configuration of the fixing screw 6 is not limited to the above-described one, but any desired configurations can be adopted, provided that the fixing screw 6 can be screwed into the one-end side bone plug 21 of the bone plug-attached tendon graft 2 in penetration through the through-hole 31 and has the head part capable of contacting the main body part 32 of the fixing member 3.

As materials for forming the fixing screw 6, stainless steel (more specifically, SUS304, SUS316 of JISG4303) and pure titanium (more specifically, JIST7401-1), titanium alloy (more specifically, Ti-6Al-4V, ASTMF-136 Ti-6Al-4V ELI of JIST7401-2) are preferable.

The tensile force-adjustable fixing tool 1 of the present invention for fixing the bone plug-attached tendon graft to be transplanted is capable of fixing the one-end side bone plug 21 of the tendon graft 2 by means of the fixing member 3 and the fixing screw 6 without using the tibia-side bone tunnel 8 (inner surface of bone tunnel) and the pulling member 22. Thereby the tensile force-adjustable fixing tool 1 is capable of decreasing deviation of the fixing position of the one-end side bone plug 21 to a smaller extent than the case in which the one-end side bone plug 21 is fixed by inserting the fixing screw for fixing the tendon graft inside the bone tunnel or the expandable fixing apparatus for fixing the tendon graft between the tibia-side bone tunnel 8 and the tibia-side bone plug 21. That is, the fixing tool 1 is capable of fixing the one-end side bone plug 21 at an initial tensile force intended by an operator.

The fixing appliance, of the present invention for fixing the bone plug-attached tendon graft to be transplanted, which is used in performing the ligament reconstruction operation is described below.

The fixing appliance of the present invention used in a ligament reconstruction operation includes a fixing tool for fixing a bone plug attached to at least one end of a tendon graft inside a bone tunnel formed at a portion where the tendon graft is to be transplanted and other end of the tendon graft is fixed and a striking tool 4 for striking the fixing tool into the bone.

The construction of the fixing tool 1 for fixing the bone plug-attached tendon graft is as described above.

The striking tool 4 has a shaft part 43 extended in a predetermined length; a fixing member-gripping part 41, provided at a distal end of the shaft part 43, for removably gripping the main body part 32 of the fixing member 3; and a proximal end portion 44b for being hammered which is provided at a proximal end of the shaft part 43.

The striking tool 4 further includes a cylindrical member 42 accommodating the shaft part 43 therein with the fixing member-gripping part 41 in exposure; and an operation part 44, which is disposed at a proximal side of the cylindrical member 42 and has the drivable portion (proximal end portion 44b), for operating mounting and removal of the fixing member 3 to be performed by the fixing member-gripping part 41.

The fixing member-gripping part 41 has a pair of opposed gripping claws 41a and 41b capable of approaching to each other and moving away from each other. The shaft part 43 has a first screwing portion 43a provided at its proximal portion. The operation part 44 has a second screwing portion 44a capable of engaging the first screwing portion 43a.

Figure 11:
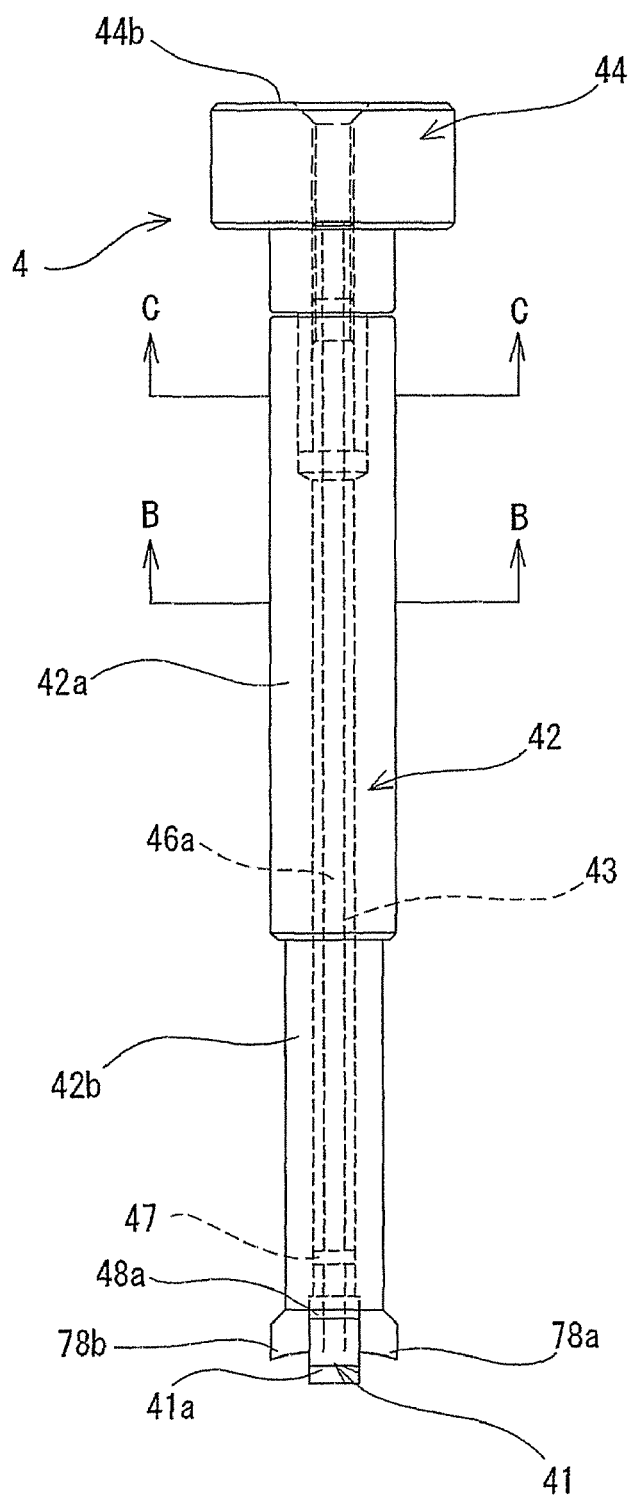
FIG. 11 is a front view of a striking tool to be used for a fixing appliance of an embodiment of the present invention.
Figure 12:
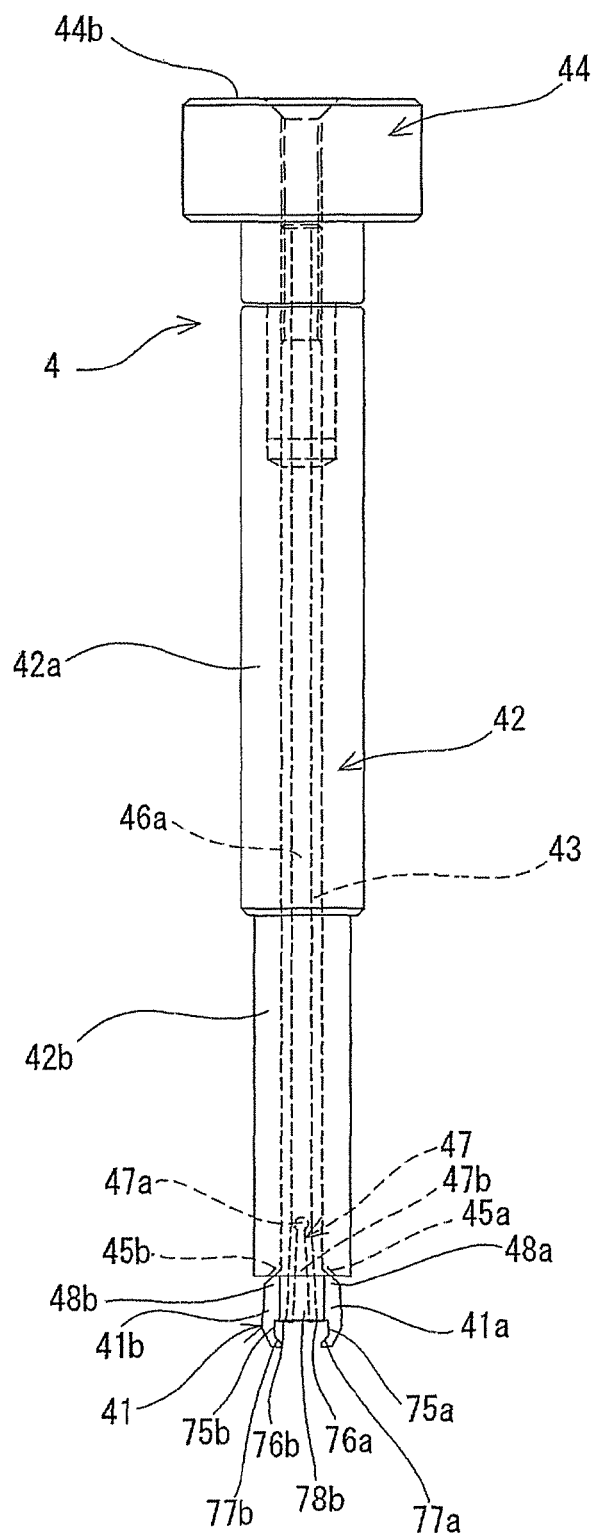
FIG. 12 is a left-hand side view of the striking tool shown in FIG. 11.
Figure 13:
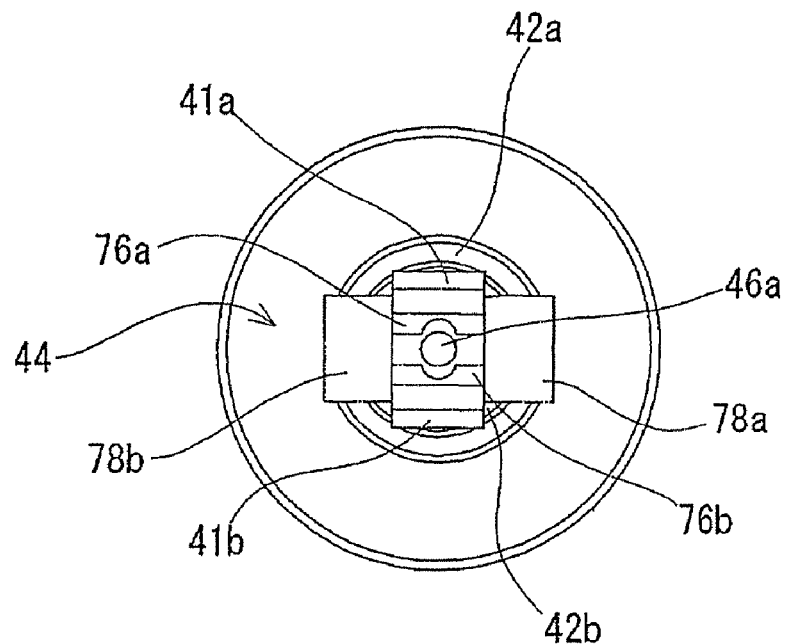
FIG. 13 is an enlarged bottom view of the striking tool shown in FIG. 11.
Figure 14:
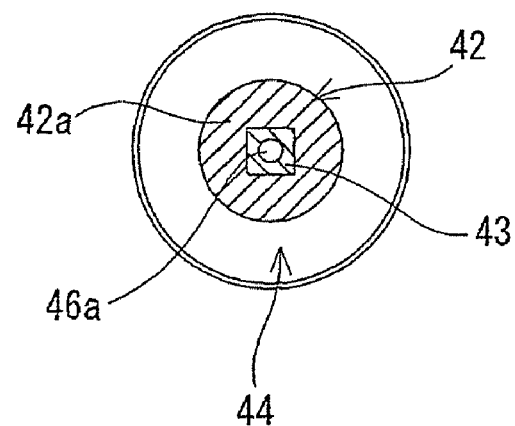
FIG. 14 is a sectional view of the striking tool taken along a line B-B of FIG. 11.
Figure 15:
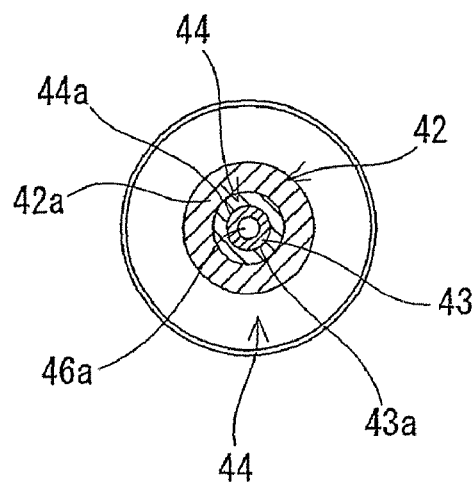
FIG. 15 is a sectional view of the striking tool taken along a line C-C of FIG. 11.

As shown in FIGS. 11 through 13, the cylindrical member 42 has a large-diameter portion 42a, formed in the shape of a column, which is held with an operator's hand when the fixing tool 1 is stricken into the bone; and a small-diameter portion 42b, formed in the shape of a column, which has a smaller diameter than the large-diameter portion 42a. The length of the cylindrical member (large-diameter portion 42a and small-diameter portion 42b) 42 is favorably 10 to 16 cm and more favorably 11 to 15 cm. The length of the large-diameter portion 42a is favorably 5 to 10 cm and more favorably 6 to 9 cm. The diameter of the large-diameter portion 42a is favorably 1.6 to 2.0 cm and more favorably 1.7 to 1.9 cm. The diameter of the small-diameter portion 42b is favorably 1.2 to 1.6 cm and more favorably 1.3 to 1.5 cm. The large-diameter portion 42a of this embodiment is disposed at the proximal side (proximal side of the small-diameter portion 42b) of the cylindrical member 42, but the large-diameter portion 42a may be disposed at the distal side of the cylindrical member 42, and the small-diameter portion 42b may be disposed at the proximal side thereof. The cylindrical member 42 may have the large-diameter portion entirely. It is preferable to knurl the side surface of the large-diameter portion 42a. Thereby it is possible to prevent the large-diameter portion 42a from slipping when the fixing tool 1 is stricken into the bone. The cylindrical member 42 is hollow from the distal end of the small-diameter portion 42b thereof to the proximal end of the large-diameter portion 42a thereof. Thereby the cylindrical member 42 is capable of axially slidably accommodating the shaft part 43 which will be described later. As shown in FIGS. 11, 12, 14, and 15, in a lumen through which the cylindrical member 42 penetrates, the proximal side of the lumen accommodated in the operation part 44 is columnar, whereas portions of the lumen other than the proximal side thereof is square pillar-shaped. Thereby the cylindrical member 42 non-rotatably accommodates the shaft part (fixing member-gripping part 41) 43 therein.

Figure 21:
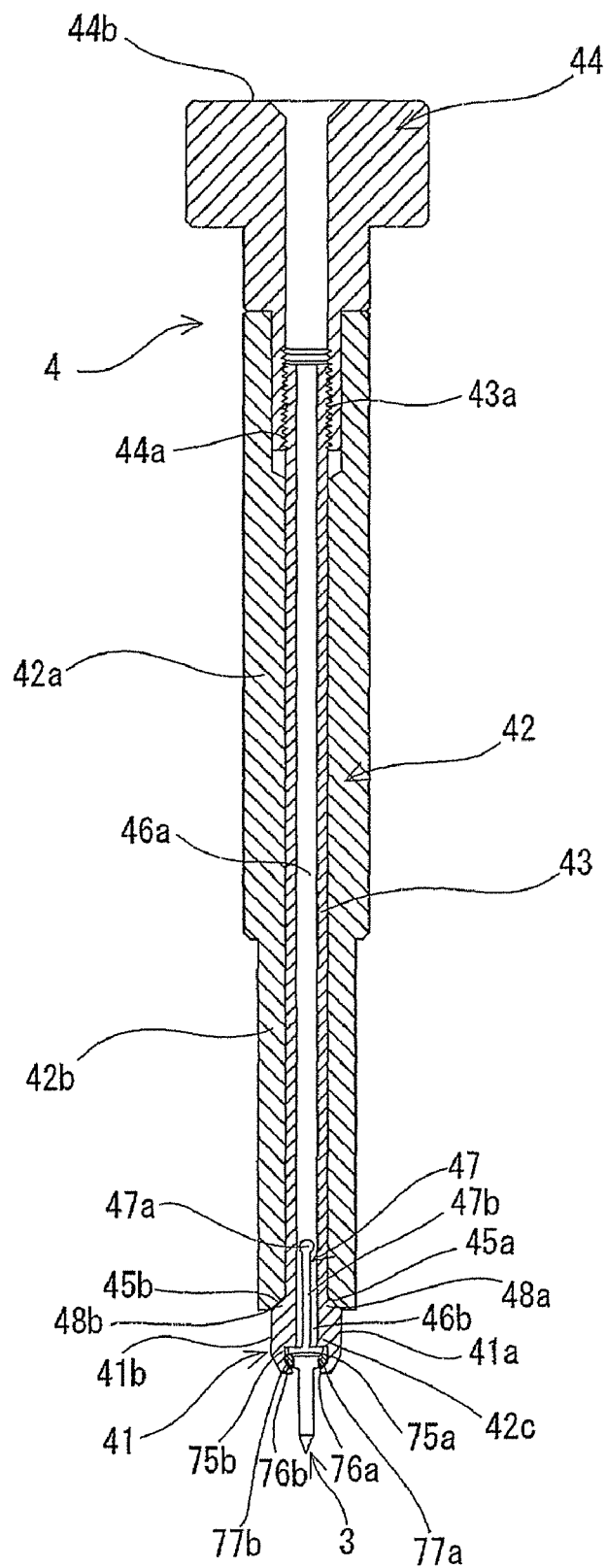
FIG. 21 is a sectional view taken along a line D-D of FIG. 18.

As shown in FIG. 21, an open portion of the small-diameter portion 42b has fit-in grooves 45a, 45b whose width become gradually larger toward the open end thereof. It is preferable to set the inclination of the fit-in grooves 45a, 45b to about 45° to the axis of the cylindrical member 42.

Figure 18:
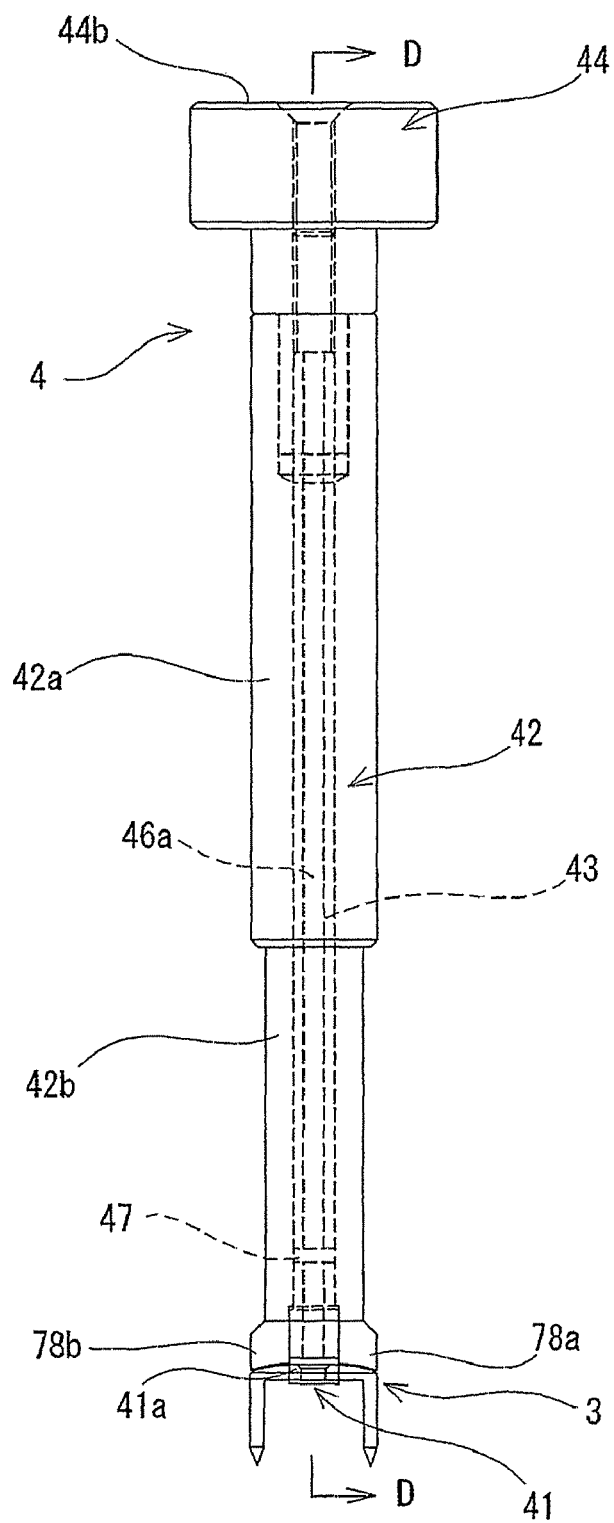
FIG. 18 is a front view showing a state in which the striking tool grips the fixing member.

As shown in FIGS. 11, 12, 13, 18, 19, and 20, the distal end of the cylindrical member 42 is provided with a pair of portions 78a, 78b, for holding the flat surface of the fixing member, facing each other. As shown in FIGS. 11 and 18, opposed sides of the cylindrical member 42 disposed at the distal side thereof are projected toward the distal end thereof. In a state where the fixing member 3 can be gripped (described later), the portions 78a, 78b for holding the flat surface of the fixing member 3 are capable of contacting portions in the neighborhood of both sides (left-hand and right-hand side edges) of the flat-surface of the main body part 32 of the fixing member 3. A gap capable of accommodating the fixing member-gripping part 41 that will be described later is formed between the portions 78a, 78b for holding the flat surface of the fixing member 3.

Figure 17:
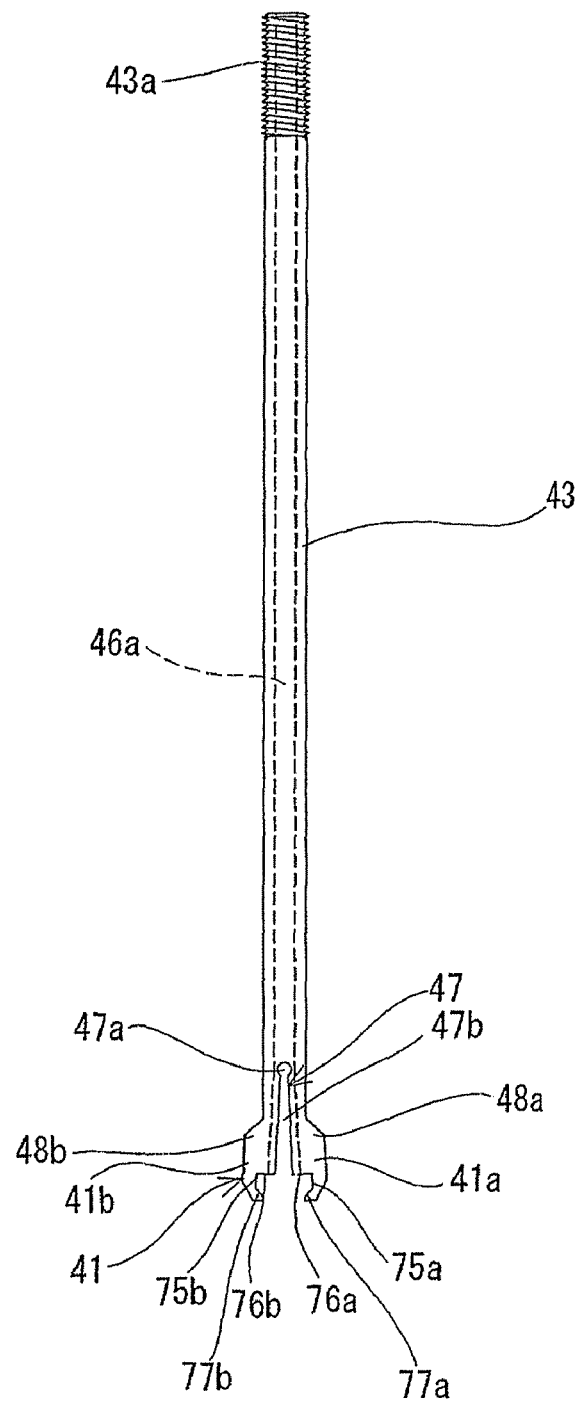
FIG. 17 is a left-hand side view of a portion of the striking tool, shown in FIG. 11, for gripping the fixing member (shaft part).

As shown in FIG. 17, the shaft part 43 has the first screwing portion 43a provided at a side in the neighborhood of the proximal end thereof and the fixing member-gripping part 41 provided at the distal end thereof. As shown in FIGS. 11, 12, 14, and 15, the shaft part 43 is axially slidably accommodated inside the cylindrical member 42. The shaft part 43 of this embodiment is formed in the shape of a square pillar except the proximal side (first screwing portion 43a) thereof. Thereby the shaft part 43 does not rotate inside the cylindrical member 42. The shaft part 43 may have any desired configurations, provided that it is axially slidable and prevented from rotating inside the cylindrical member 42.

A one-end side gripping claw 41a and other-end side gripping claw 41b are provided at a distal portion of the shaft part 43. The one-end side gripping claw 41a and the other-end side gripping claw 41b constitute the fixing member-gripping part 41 which removably grips the main body part 32 of the fixing member 3. The fixing member-gripping part 41 is axially slidable with the fixing member-gripping part 41 being sandwiched between the portions 78a, 78b, for holding the flat surface of the fixing member 3, provided at the distal end of the cylindrical member 42. The one-end side gripping claw 41a and the other-end side gripping claw 41b are so formed as to confront each other. As shown in FIGS. 12 and 17, the one-end side gripping claw 41a has a surface 75a for gripping the side of the fixing member 3, a surface 76a for sandwiching the flat surface of the fixing member 3, and a surface 77a for gripping the bottom portion of the fixing member 3. Similarly the other-end side gripping claw 41b has a surface 75b for gripping the side of the fixing member 3, a surface 76b for sandwiching the flat surface of the fixing member 3, and a surface 77b for gripping the bottom portion of the fixing member 3. Between the one-end side gripping claw 41a and the other-end side gripping claw 41b, there is provided a gap into which the fixing member 3 can be inserted from the axial distal end of the striking tool 4. In this embodiment, the fixing member-gripping part 41 has the shape of a pair of hooks disposed in confrontation.

A cut-away portion 47 is formed on the fixing member-gripping part 41 (the one-end side gripping claw 41a and the other-end side gripping claw 41b). The cut-away portion 47 has a columnar cut-away portion 47a penetrating through the one-end side gripping claw 41a and the other-end side gripping claw 41b (or the proximal side of the one-end side gripping claw 41a and that of the other-end side gripping claw 41b) toward the side surface of the fixing member-gripping part 41 in the shape of a column and a groove-shaped cut-away portion 47b extended widely in the direction of the one-end side gripping claw 41a and the other-end side gripping claw 41b from the columnar cut-away portion 47a toward the distal end of the fixing member-gripping part 41. The cut-away portion 47 allows the one-end side gripping claw 41a and the other-end side gripping claw 41b to be movable (elastically deformable) in the direction in which the one-end side gripping claw 41a and the other-end side gripping claw 41b approach each other and moves away from each other (deformation toward the center and away therefrom).

As shown FIGS. 18 through 21, when the one-end side gripping claw 41a and the other-end side gripping claw 41b elastically deform in the direction in which they approach each other (toward the center), the one-end side surface 75a for gripping the side of the fixing member 3 and the other-end side surface 75b for gripping the side of the fixing member 3 move in the direction in which they approach each other (toward the center), and the one-end side surface 77a for gripping the bottom portion of the fixing member 3 and other-end side surface 77b for gripping the bottom portion of the fixing member 3 also move in the direction in which they approach each other (toward the center). In this state, the surfaces 75a and 75b for gripping the side of the fixing member 3, the surfaces 77a and 77b for gripping the bottom portion of the fixing member 3, and the portions 78a and 78b for holding the flat surface of the fixing member 3 contact the main body part 32 of the fixing member 3 respectively. Thereby the fixing member-gripping part 41 is prevented from moving in directions other than the side surface direction thereof, which places the fixing member 3 in a state where the fixing member-gripping part 41 is capable of gripping the fixing member 3.

The fixing member-gripping part 41 is larger than the shaft part 43. The proximal portions 48a, 48b of the fixing member-gripping part 41 incline in such a way that the width of the proximal-end surfaces thereof become gradually smaller toward the proximal end of the shaft part 43. In other words, the proximal-end surface of each of the proximal portions 48a, 48b of the fixing member-gripping part 41 inclines toward the proximal end of the shaft part 43 and the axis thereof. It is preferable that the inclination of the proximal-end surface of each of the proximal portions 48a, 48b is almost equal to that of the fit-in grooves 45a, 45b. Thereby the proximal portions 48a, 48b of the fixing member-gripping part 41 can be accommodated in the fit-in grooves 45a, 45b (inside the cylindrical member 42) of the cylindrical member 42 respectively. The one-end side gripping claw 41a and the other-end side gripping claw 41b are capable of moving (elastically deforming) in the direction (toward the center) in which they approach each other by accommodating the proximal portions 48a, 48b in the fit-in grooves 45a, 45b respectively.

As shown in FIG. 17, the first screwing portion 43a capable of engaging the second screwing portion 44a of the operation part 44 which is described later is formed at the side in the neighborhood of the proximal end of the shaft part 43.

Figure 16:
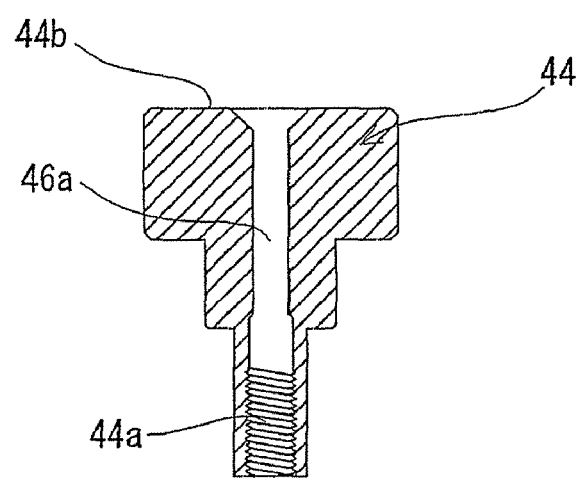
FIG. 16 is a sectional view of an operation part of the striking tool shown in FIG. 11.

As shown in FIG. 16, the cylindrical member 42 has the operation part 44 disposed at the proximal end thereof. It is possible to strike the fixing member 3 gripped by the striking tool 4 (fixing member-gripping part 41) into the tibia 10 by hitting the proximal end portion 44b (proximal-end surface) provided at the proximal end of the operation part 44 with an unshown hammer or the like. The operation part 44 has a proximal side having a larger diameter than that of the large-diameter portion 42a of the cylindrical member 42 and a distal side having a smaller diameter than that of the large-diameter portion 42a. Thus the operation part 44 is nut-shaped. The diameter of the operation part 44 at the proximal side thereof is set to favorably 2 cm to 5 cm and especially favorably 3 cm to 4 cm. The operation part 44 is hollow from the distal end thereof to the proximal end thereof. The second screwing portion 44a capable of engaging the first screwing portion 43a of the shaft part 43 is formed on the inner surface of the operation part 44 at the distal side thereof. The distal side of the operation part 44 is accommodated in the proximal side of the cylindrical member 42 with the second screwing portion 44a engaging the first screwing portion 43a of the shaft part 43. Therefore by rotating (rotating the operation part 44 in the tightening direction) the operation part 44, the shaft part 43 (and the fixing member-gripping part 41) move to the proximal side of the striking tool 4 owing to the progress of the engagement between the first screwing portion 43a and the second screwing portion 44a. In other words, it engages the shaft part 43 inside the cylindrical member 42 owing to the rotation of the operation part 44, thus holding the shaft part 43 (and the fixing member-gripping part 41) movably to the proximal side of the striking tool 4. By rotating the operation part 44 reversely (by rotating the operation part 44 in removal direction), the engagement between the first screwing portion 43a and the second screwing portion 44a regresses. Thereby the shaft part 43 (and the fixing member-gripping part 41) can be moved to the distal side of the striking tool 4.

As shown in FIGS. 18 through 21, owing to a movement of the cylindrical member 42 to the proximal side of the striking tool 4, a pair of the gripping claws 41a and 41b of the fixing member-gripping part 41 becomes proximate to each other to allow the gripping claws 41a and 41b to grip the fixing member 3. More specifically, by moving the fixing member-gripping part 41 to the proximal side of the cylindrical member 42, the proximal portions 48a, 48b of the fixing member-gripping part 41 are accommodated in the fit-in grooves 45a, 45b (inside the cylindrical member 42) of the cylindrical member 42 respectively. Thereby the one-end side gripping claw 41a and the other-end side gripping claw 41b move (elastically deform) in the direction (toward the center) in which they approach each other and are placed in the state in which they are capable of gripping the fixing member 3 therebetween. Owing to the movement of the cylindrical member 42 to the distal side of the striking tool 4, a pair of the one-end side gripping claw 41a and the other-end side gripping claw 41b move away from each other. Thereby the fixing member 3 can be placed in a state in which the fixing member 3 is releasable from the fixing member-gripping part 41.

Figure 19:
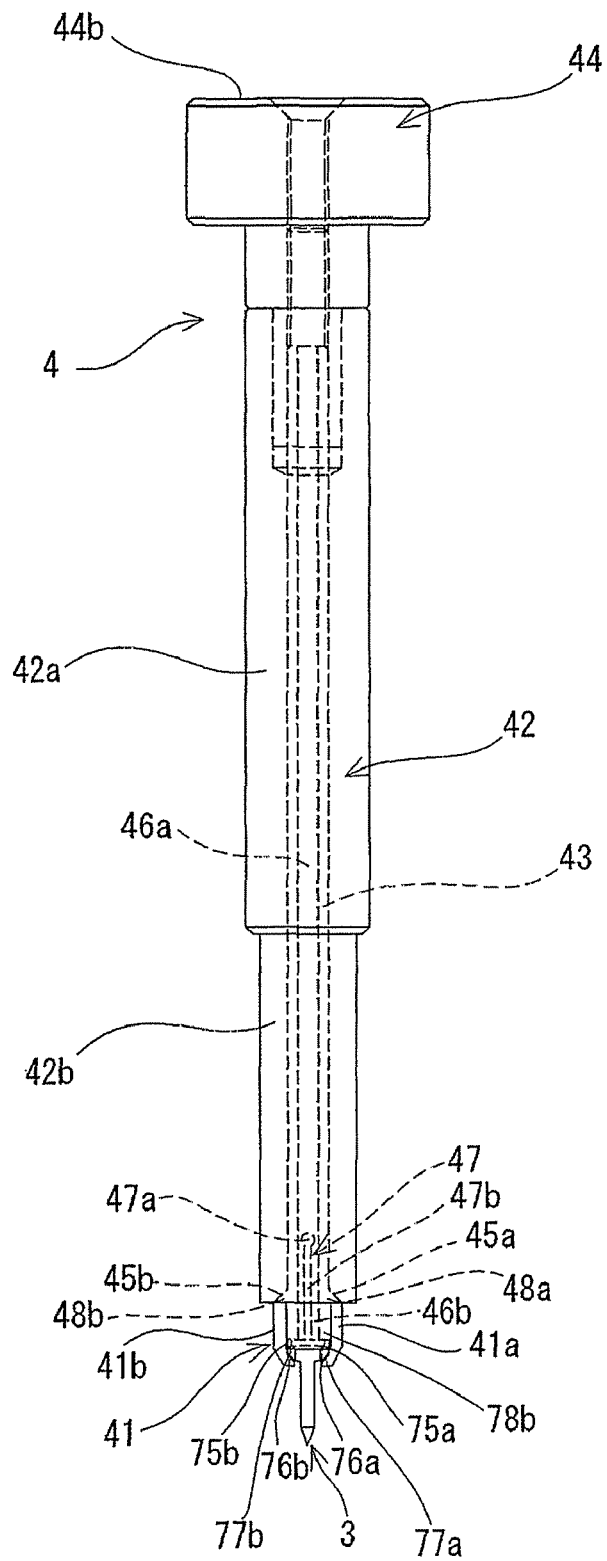
FIG. 19 is a left-hand side view showing a state in which the fixing member shown in FIG. 18 is gripped.
Figure 20:
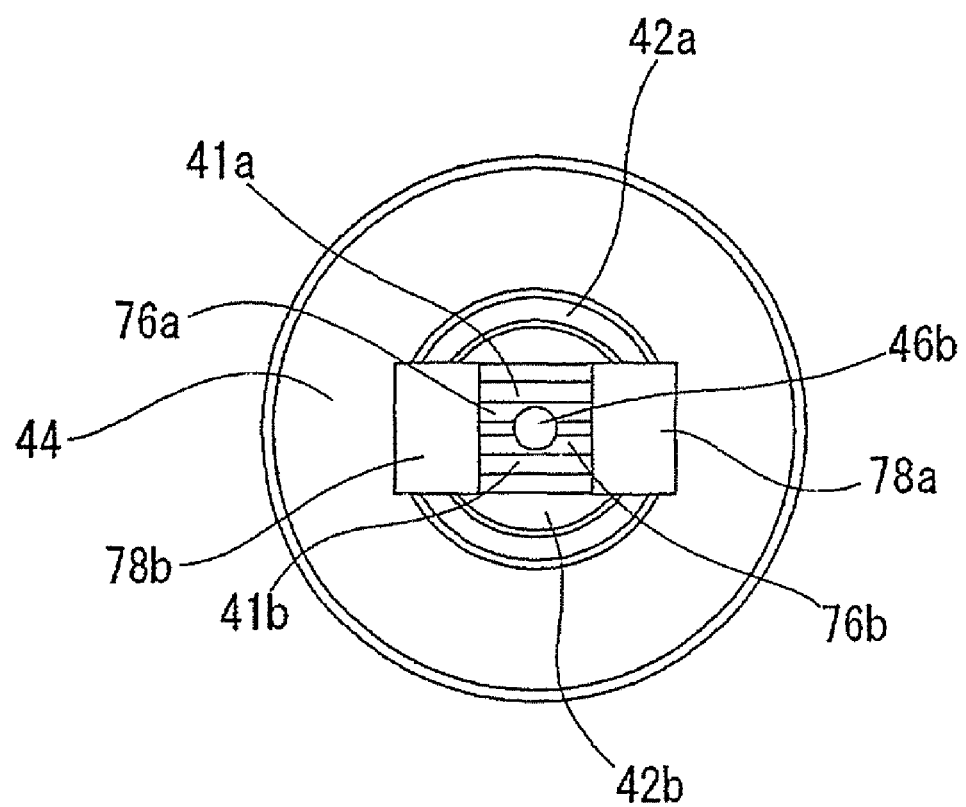
FIG. 20 is an enlarged bottom view showing a state in which the striking tool shown in FIG. 11 is capable of gripping the fixing member.

The striking tool 4 may be hollow from its distal end to its proximal end. More specifically, as shown in FIGS. 11 through 17, the striking tool 4 has a first lumen 46a penetrating therethrough from the proximal end of the cut-away portion 47 of the fixing member-gripping part 41 to the proximal end of the operation part 44 through the shaft part 43. The first lumen 46a allows a guide pin or the like to be inserted into the striking tool 4. When the fixing member-gripping part 41 is placed in the state in which it is capable of gripping the fixing member 3 (state in which the one-end side gripping claw 41a and the other-end side gripping claw 41b approach each other and elastically deform), as shown in FIGS. 19 through 21, the striking tool 4 has a second lumen 46b hollow from the surface 76a, 76b, of the fixing member-gripping part 41, for sandwiching the flat surface of the fixing member 3 to the distal end of the cut-away portion 47. In this case, the striking tool 4 is hollow from its distal end to its proximal end owing to the formation of the first lumen 46a and the second lumen 46b and the cut-away portion 47 orthogonal to the first lumen 46a and to the second lumen 46b. The guide pin or the like can be inserted into the striking tool 4 when the fixing member-gripping part 41 is placed in the state in which the fixing member-gripping part 41 is capable of gripping the fixing member 3.

It is preferable that the fixing tool, for fixing the bone plug-attached tendon graft to be transplanted, which is used in the ligament reconstruction operation has a pilot hole-forming tool.

Figure 22:
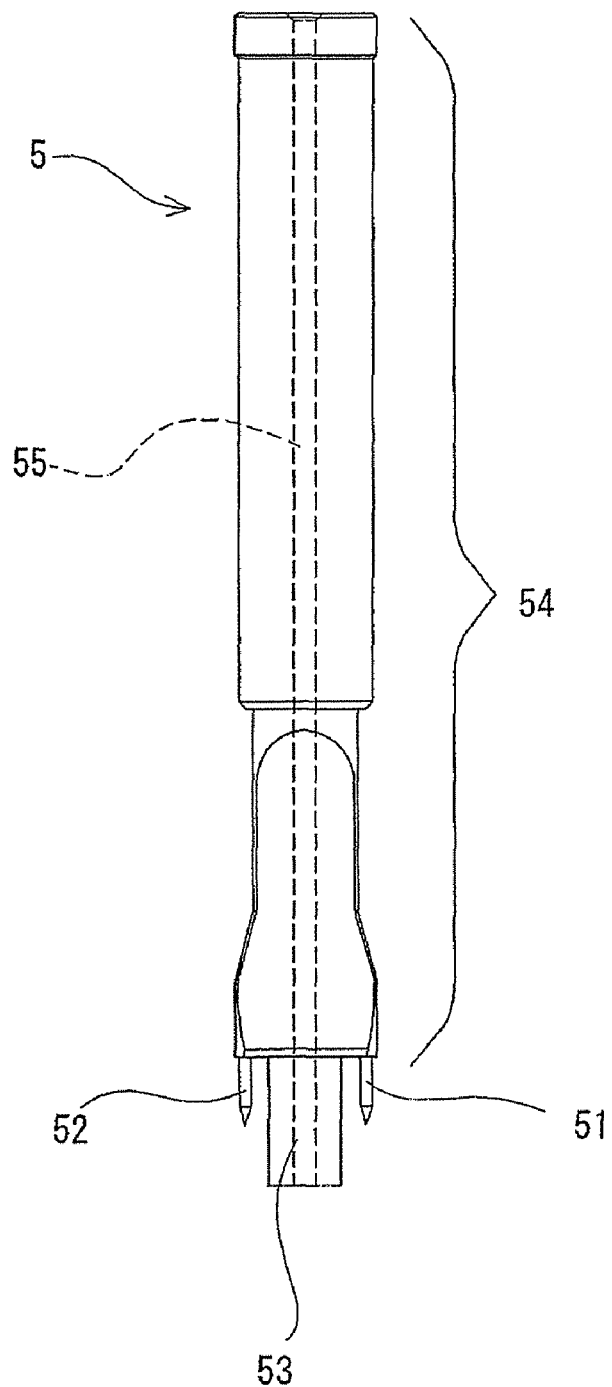
FIG. 22 is a front view of a pilot hole-forming tool used for a fixing appliance of an embodiment of the present invention.
Figure 23:
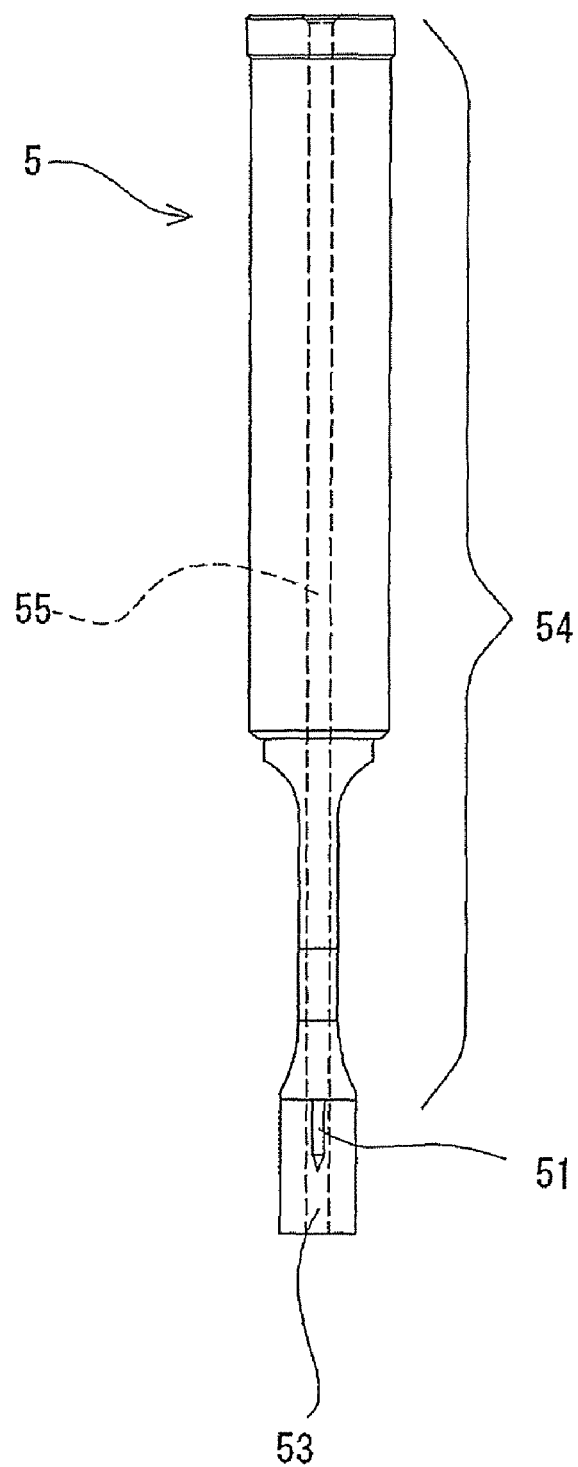
FIG. 23 is a right-hand side view of the pilot hole-forming tool shown in FIG. 22.
Figure 24:
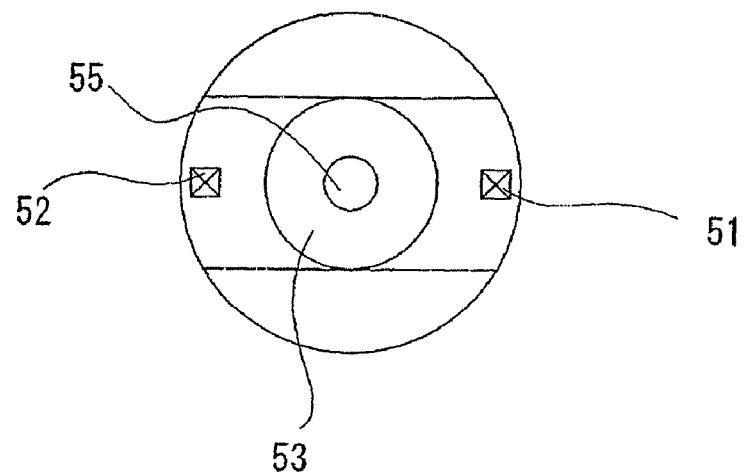
FIG. 24 is an enlarged bottom view of the pilot hole-forming tool shown in FIG. 22.
Figure 25:
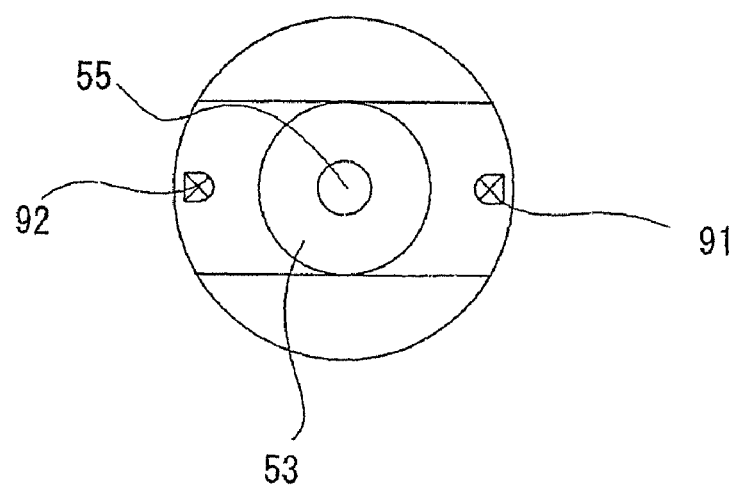
FIG. 25 is a bottom view of a pilot hole-forming tool of another example.

FIG. 22 is a front view of a pilot hole-forming tool used for a fixing appliance of an embodiment of the present invention. FIG. 23 is a right-hand side view of the pilot hole-forming tool shown in FIG. 22. FIG. 24 is an enlarged bottom view of the pilot hole-forming tool shown in FIG. 22. FIG. 25 is a bottom view of a pilot hole-forming tool of another example.

A pilot hole-forming tool 5 has a shaft part 54; a projected part 53 to be penetrated into the bone tunnel, formed at a distal end of the shaft part 54, which has an outer diameter almost equal to an inner diameter of the formed bone tunnel; and two needle-shaped parts 51, 52 formed at a distal end of the shaft part 54 by spacing the needle-shaped parts 51, 52 at an interval equal to that between the spike parts 33 and 34 with the needle-shaped parts 51, 52 sandwiching the projected part 53 to be penetrated into the bone tunnel therebetween.

The shaft part 54 of this embodiment is formed in the shape of a column at its proximal side and approximately square pillar-shaped (plate-shaped) at its distal side. It is preferable to knurl the side surface of the shaft part 54. Thereby it is possible to prevent the pilot hole-forming tool 5 from sliding when the pilot hole-forming tool 5 is stricken into the bone. It is preferable to set the length of the shaft part 54 to 11 to 16 cm.

The projected part 53 to be entered into the bone tunnel is projected from the distal end of the shaft part 54 and formed in the shape of columnar. The configuration of the projected part 53 is not limited to be columnar, but the projected part to be penetrated into the bone tunnel may have the shape of an elliptic pillar or a chamfered polygon. It is preferable to set the outer diameter of the projected part to be penetrated into the bone tunnel almost equally to the inner diameter of the tibia-side bone tunnel.

The needle-shaped parts 51, 52 are provided to form pilot holes 56, 57 into which two spike parts 33, 34 of the fixing member 3 are penetrated. The two needle-shaped parts 51, 52 are formed in parallel with each other and also with the projected part 53. The two needle-shaped parts 51, 52 are spaced at an interval equal to that between the two spike parts 33, 34 of the fixing member 3 with the needle-shaped parts 51, 52 sandwiching the projected part 53 therebetween. In other words, the projected part 53 is disposed at the center of the interval between the needle-shaped parts 51 and 52 spaced at the interval equal to that between the two spike parts 33, 34 of the fixing member 3. It is preferable that the length of each of the needle-shaped parts 51 and 52 is equal to that of the spike of the fixing member 3 or a little shorter than that of the spike thereof. More specifically, it is preferable to set the length of each of the needle-shaped parts 51, 52 to favorably 7 to 12 cm. It is preferable to set the width of each of the needle-shaped parts 51, 52 equally to or a little shorter than that of the spike parts 33, 34 of the fixing member 3. More specifically, it is preferable to set the width of each of the needle-shaped parts 51, 52 to 1.4 to 2.0 mm. The distal end of each of the needle-shaped parts 51, 52 is pointed so that the needle-shaped parts 51, 52 can be pierced into the tibia 10. As the form of the distal portion of the needle-shaped parts 51, 52, conic, three-sided pyramidal, and four-sided pyramidal configurations are listed. It is preferable that portions of the needle-shaped parts 51, 52 other than the distal portion thereof are columnar, triangular prism-shaped or square pillar-shaped. As the configuration of the needle-shaped parts 51, 52 of this embodiment, the distal portion thereof has the shape of a four-sided pyramid, whereas portions thereof other than the distal portion thereof has the shape of a square pillar. The configuration of the needle-shaped parts 51, 52 is not limited to the above-described one, but the configuration of the inner side thereof and that of the outer side thereof may be different from each other. For example, as shown in FIG. 25, it is preferable that the opposed inner sides of needle-shaped parts 91, 92 do not substantially have a corner but have a curved surface. The inner side of each of the needle-shaped parts 91, 92 does not have a corner but is columnar, whereas the outer side of each of the needle-shaped parts 91, 92 has a corner and thus the shape of a square pillar. Thereby it is possible to decrease the extent of an impact to be imparted to the wall of the tibia-side bone tunnel when the needle-shaped parts 91, 92 are stricken into the tibia 10.

The pilot hole-forming tool 5 may be hollow from its distal end to its proximal end. In this embodiment, the pilot hole-forming tool 5 has a lumen 55 penetrating the pilot hole-forming tool 5 from the distal end of the projected part 53 to the proximal end of the shaft part 54. The lumen 55 allows the guide pin or the like to be inserted into the pilot hole-forming tool 5.

The ligament reconstruction method to be carried out by using the tendon graft to be transplanted having the bone plug at its both ends is described below.

In the ligament reconstruction method of the present invention, the following steps are performed: a step of preparing the tendon graft 2 to be transplanted having the bone plug at both ends thereof; a step of mounting the pulling members 22, 26 on bone plugs of the collected tendon graft 2 respectively; a step of forming the femur-side bone tunnel 9 and the tibia-side bone tunnel 8 on the portion to be reconstructed; a step of disposing the collected tendon graft 2 at the portion to be reconstructed in such a way that one of the bone plugs is positioned inside the tibia-side bone tunnel 8 and the other of the bone plugs is positioned inside the femur-side bone tunnel 9; a step of fixing the other side of the tendon graft 2 to the femur; a step of striking the fixing member 3 having the main body part 32 provided with the through-hole 31 formed at the central portion thereof and the two spike parts 33, 34 which extend almost parallelly from both side edges of the main body part 32 with the spike parts 33, 34 spaced at the predetermined interval longer than the diameter of the tibia-side bone tunnel 8 and which can be stricken into the tibia into a portion in the neighborhood of the tibia-side bone tunnel 8 in such a way that the main body part 32 crosses the opening of the bone tunnel; a step of piercing the guide pin 85 to one of the bone plugs; a step of disposing the fixing screw 6 including the shaft part 65 having the self-tap portion 63 and the male screw portion 62 both of which can be penetrated through the through-hole 31 of the fixing member 3 and are screwed into the bone plug, the head part 61 which is disposed at the proximal end of the shaft part 65 and can be brought into contact with the main body part 32 on the peripheral edge of the through-hole 31 of the fixing member 3, and the lumen 66 which is extended from the proximal end of the head part 61 to the distal end of the shaft part 65 and through which the guide pin 85 can be penetrated in such a way that the guide pin 85 penetrates through the lumen 66 of the fixing screw 6 and that the fixing screw 6 is advanced along the guide pin 85 to penetrate the guide pin 85 through the through-hole 31 of the fixing member 3 and bring the distal end of the fixing screw 6 into contact with one of the bone plugs; a step of screwing the fixing screw 6 into one of the bone plugs; a step of pulling the pulling member 22 mounted on one of the bone plugs and extended from the gap between the main body part 32 of the fixing member 3 and the opening of the tibia-side bone tunnel 8 and measuring a pulling-caused tensile force applied to the pulling member 22; a step of progressing screwing of the fixing screw 6 into one of the bone plugs and bringing the head part 61 of the fixing screw 6 into contact with the fixing member 3; and a tensile force-adjusting step of adjusting the tensile force applied to the pulling member 22 by progressing the screwing of the fixing screw 6 into one of the bone plugs till the tensile force applied to the pulling member 22 being measured attains a predetermined value after the head part 61 of the fixing screw 6 contacts the fixing member 3.

An embodiment in which the ligament reconstruction method of the present invention is utilized for a cruciate ligament reconstruction method is described below.

The anterior cruciate ligament reconstruction method to be carried out by using the bone plug-attached tendon graft to be transplanted is described below with reference to FIG. 29 through 37.

Figure 38:
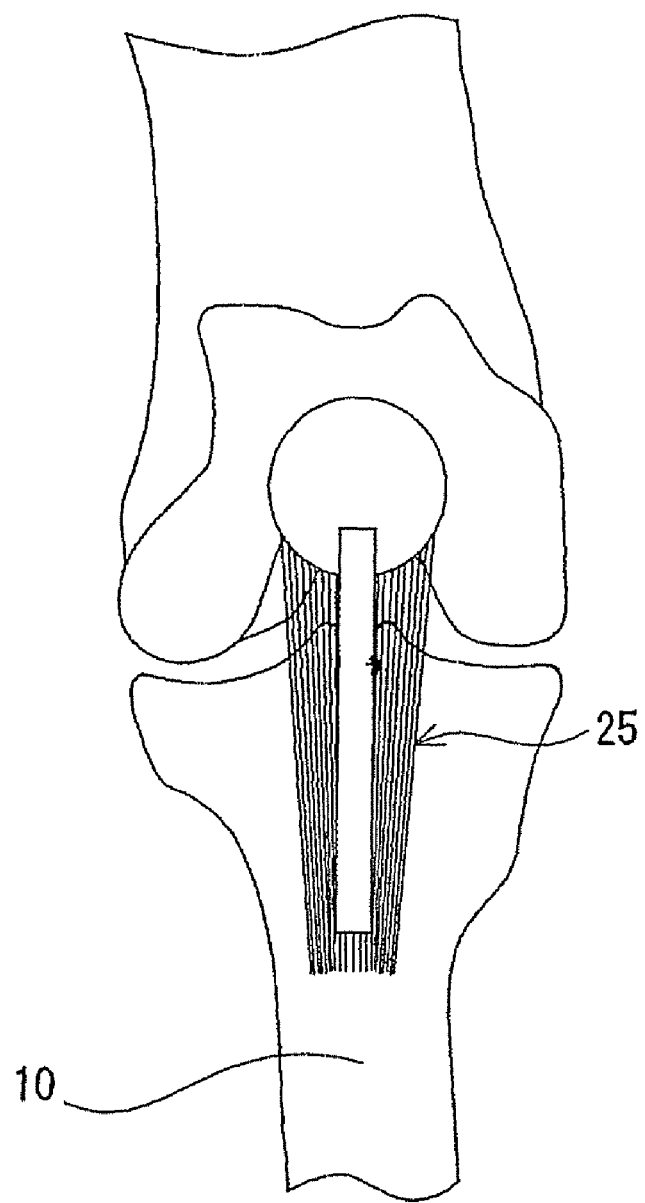
FIG. 38 is an explanatory view for explaining the tendon graft having the bone plug used in the anterior cruciate ligament reconstruction method of the present invention.
Figure 39:
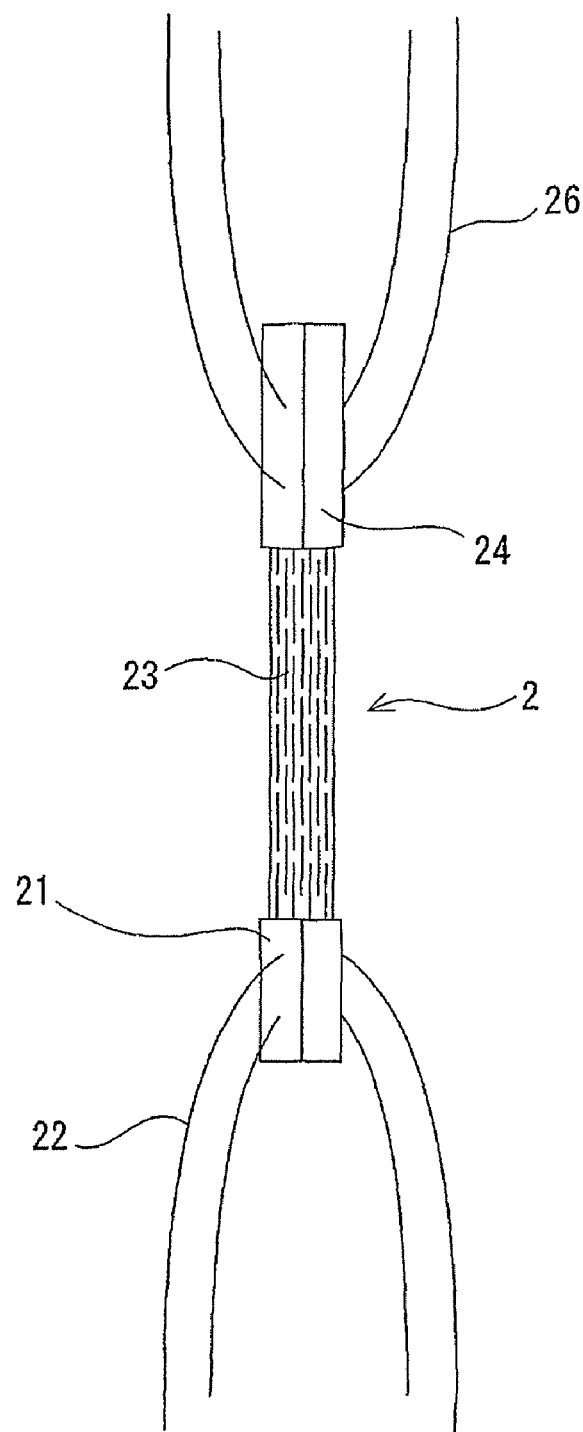
FIG. 39 is an explanatory view for explaining the tendon graft having the bone plug used in the anterior cruciate ligament reconstruction method of the present invention.

Initially the step of preparing the tendon graft 2 having the bone plug at its both ends is performed. For example, as shown in FIG. 38, a portion in the neighborhood of the center of a patellar tendon 25 is collected widthwise in the range of 8 to 14 mm. A bone plug having a length of 10 to 25 mm and a width of 8 to 14 mm is attached to each widthwise end of the patellar tendon 25 to form a bone plug-attached free ligament tendon graft to be transplanted. In this embodiment, the bone plug-attached tendon graft 2 is collected from the patellar tendon. As described later, when the bone plug-attached tendon graft 2 has only the one-end side bone plug 21, it is possible to use a bone plug-attached quadriceps femoris tendon or the like as the tendon graft to be transplanted.

Thereafter the step of mounting the pulling members 22, 26 on each bone plug of the collected tendon graft 2 is performed. More specifically, the pulling members 22, 26 are sewed to both bone plugs (one-end side bone plug 21 and other-end side bone plug 24) of the bone plug-attached tendon graft 2 collected in the manner described above. In this embodiment, two pulling members 22 are sewed to the one-end side bone plug 21, whereas two pulling members 26 are sewed to the other-end side bone plug 24.

Figure 40:
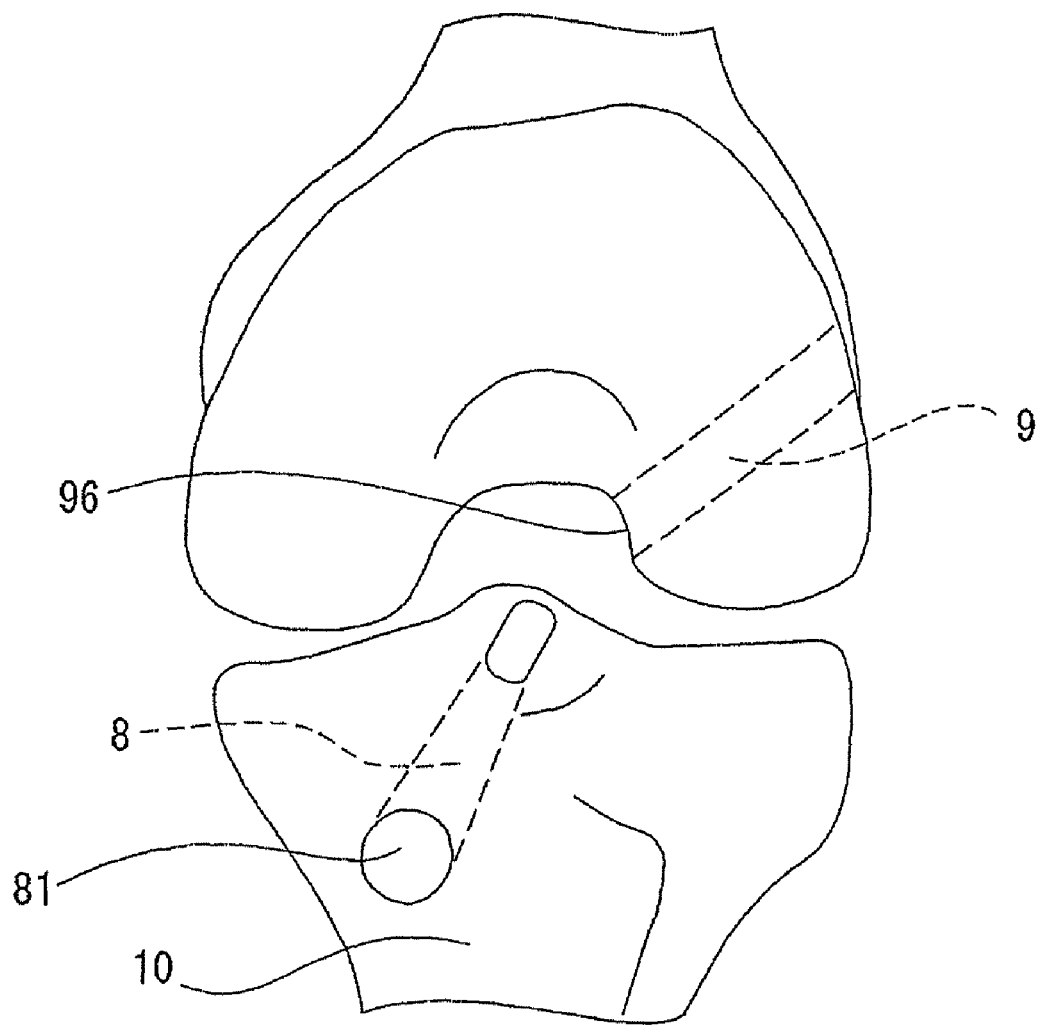
FIG. 40 is an explanatory view for explaining a bone bole formed in the anterior cruciate ligament reconstruction method of the present invention.

Thereafter the step of forming the bone tunnel in the portion to be reconstructed is performed. More specifically, as shown in FIG. 40, the femur-side bone tunnel 9 and the tibia-side bone tunnel 8 are formed at the portion to be reconstructed. The femur-side bone tunnel 9 and the tibia-side bone tunnel 8 of this embodiment are formed in the shape of a column, but may be formed in the shape of an ellipse or a square pillar. A portion in the neighborhood of an open portion (front opening) 81 of the tibia-side bone tunnel 8 may be tapered in such a way that the diameter of the tibia-side bone tunnel 8 becomes gradually larger to some extent toward the open portion (front opening) 81. Similarly a portion in the neighborhood of an open portion (upper opening) opposite to an open portion 96 (front opening) of the femur-side bone tunnel 9 may be tapered in such a way that the diameter of the femur-side bone tunnel 9 becomes gradually larger to some extent toward the open portion (upper opening). Thereby the screw or the like can be easily inserted into the bone tunnels. As the method of forming the femur-side bone tunnel 9 and the tibia-side bone tunnel 8, a known method of excavating the bone with a drill to penetrate it through a formed bone tunnel is used.

Figure 29:
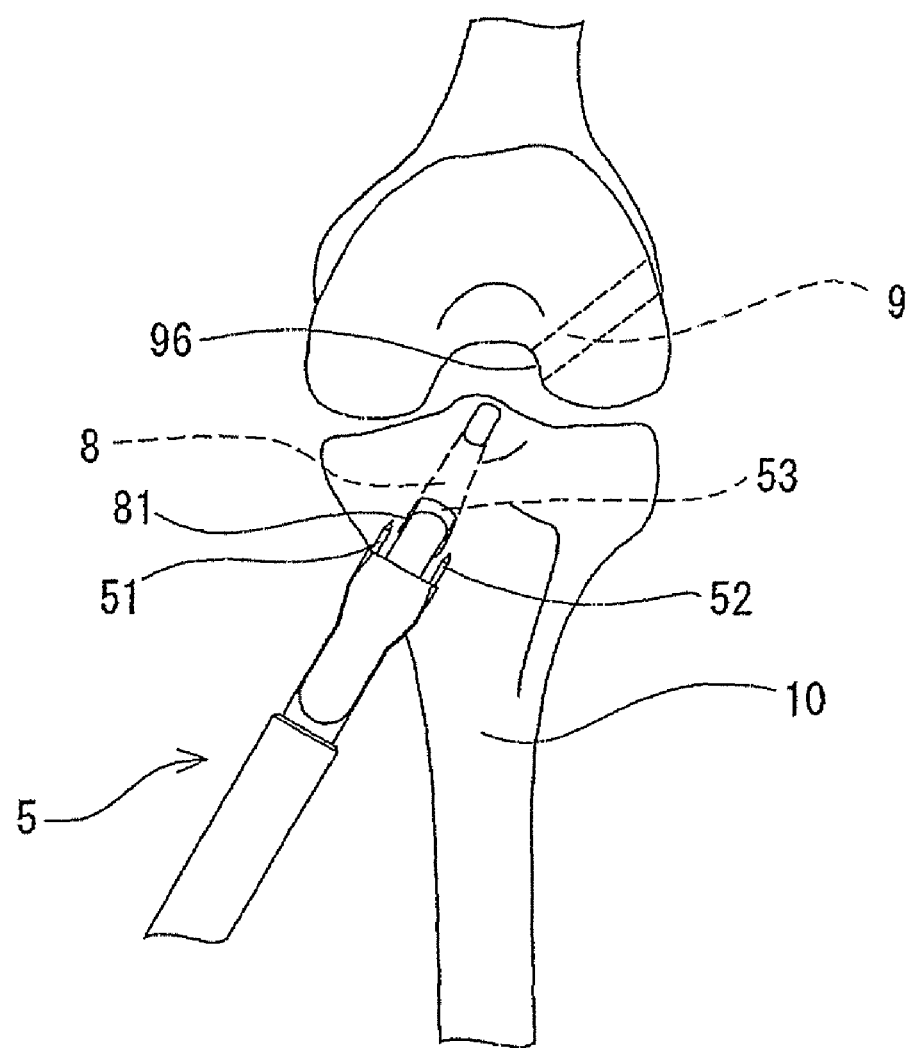
FIG. 29 is an explanatory view for explaining how a pilot hole is formed in an anterior cruciate ligament reconstruction method of the present invention in which a tendon graft having a bone plug is used.
Figure 30:
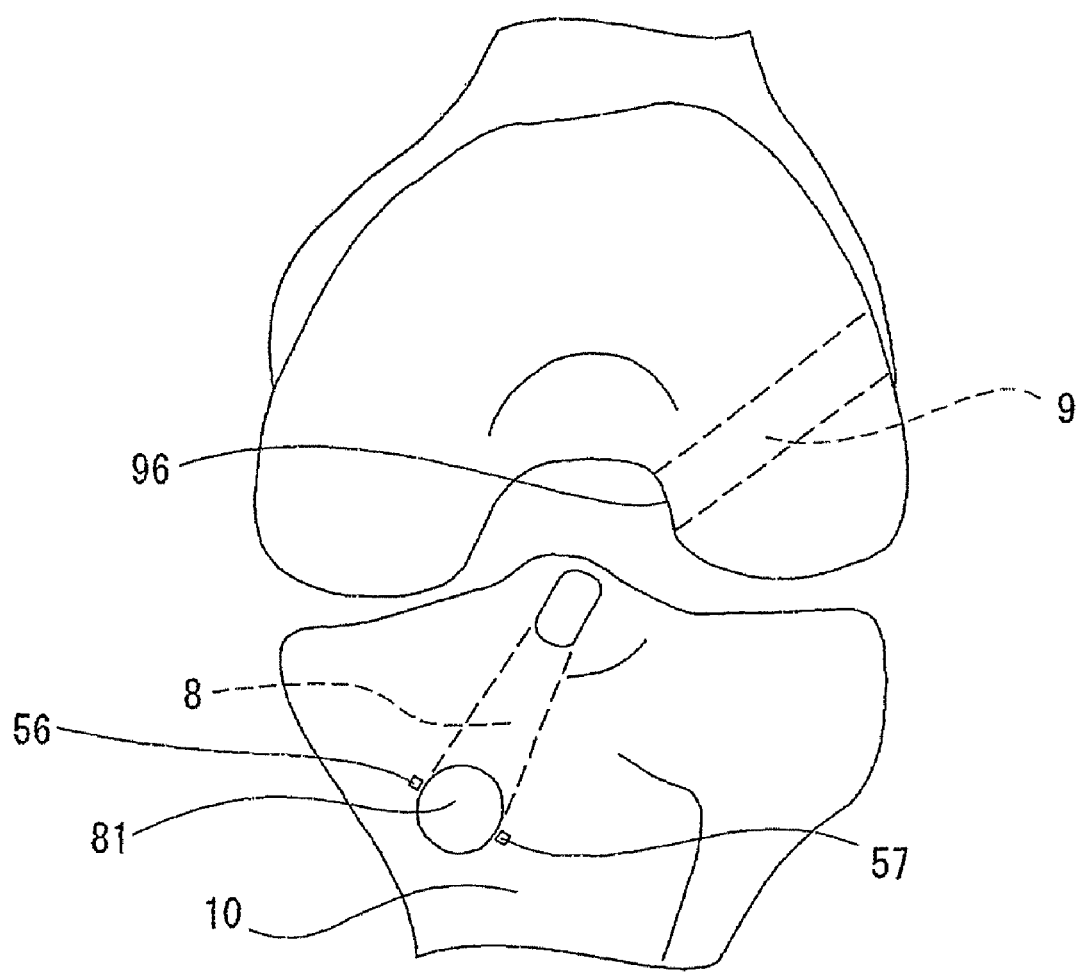
FIG. 30 is an explanatory view for explaining how the pilot hole is formed in the anterior cruciate ligament reconstruction method of the present invention.

The next step to be performed is the pilot hole-forming step of forming the pilot holes 56, 57 into which the two spike parts of the fixing member 3 penetrate in the neighborhood of the open portion 81 of the bone tunnel into which the fixing member 3 is stricken. In this embodiment, at the pilot hole-forming step of forming the pilot holes 56, 57, the pilot holes 56, 57 used to strike the fixing member 3 into the tibia 10 are formed in the neighborhood of the open portion 81 of the tibia-side bone tunnel 8 by using the pilot hole-forming tool 5. As shown in FIG. 29 or FIG. 30, the projected part 53 of the pilot hole-forming tool 5 is inserted into the tibia-side bone tunnel 8 from the open portion (front opening) 81 of the tibia-side bone tunnel 8. The proximal side of the shaft part 54 of the pilot hole-forming tool 5 is hit with an unshown hammer or the like to strike the pilot hole-forming tool 5 into the tibia 10. Thereby the needle-shaped parts 51, 52 are stricken into the tibia 10, and the pilot holes 56, 57 into which the two spike parts 33, 34 of the fixing member 3 are penetrated are formed in the neighborhood of the open portion (front opening) 81 of the tibia-side bone tunnel 8. A fixing member which will be described later may be stricken into the tibia 10 without forming the pilot holes 56, 57.

The next step to be performed is the step of disposing the collected tendon graft 2 at the portion to be reconstructed in such a way that one of the bone plugs is positioned inside the tibia-side bone tunnel 8 and that the other of the bone plugs is positioned inside the femur-side bone tunnel 9. More specifically, the other-end side bone plug 24 of the bone plug-attached tendon graft 2 is inserted into the tibia-side bone tunnel 8 from the open portion (front opening) 81 thereof. As the insertion of the other-end side bone plug 24 into the tibia-side bone tunnel 8 progresses, the other-end side bone plug 24 advances inside the tibia-side bone tunnel 8 and thereafter projects from the open portion (femur-side open portion) opposite to the open portion (front opening) 81, thus penetrating into the gap between the tibia 10 and the femur (inside joint). As the insertion of the other-end side bone plug 24 is further progressed, the other-end side bone plug 24 is inserted into the femur side bone tunnel 9 from the open portion (front opening) 96. By moving the bone plug-attached tendon graft (other-end side bone plug 24) 2 to the femur side, the one-end side bone plug 21 is inserted into the tibia-side bone tunnel 8 from the open portion (front opening) 81. Thereby the one-end side bone plug 21 is disposed inside the tibia-side bone tunnel 8, whereas the other-end side bone plug 24 is disposed inside the femur side bone tunnel 9.

Figure 31:
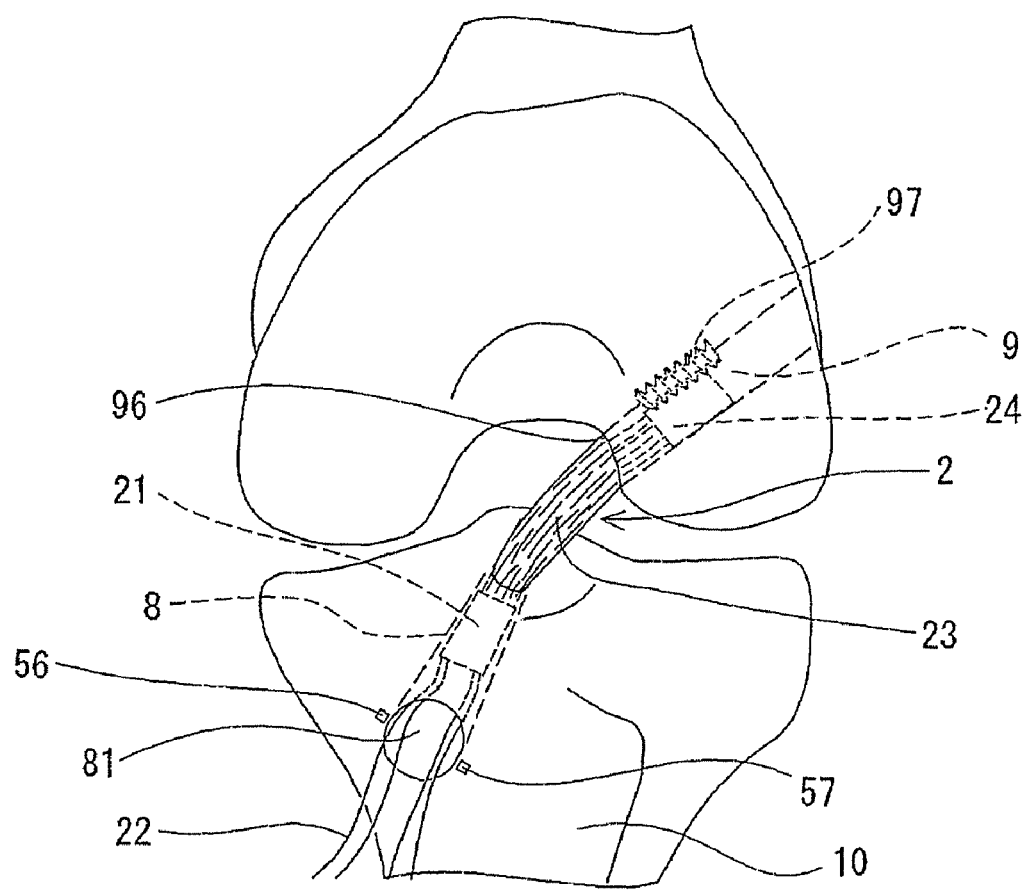
FIG. 31 is an explanatory view for explaining how the tendon graft is disposed at a predetermined position and how the tendon graft is fixed to a femur side in the anterior cruciate ligament reconstruction method of the present invention.

Thereafter the step of fixing the other side of the tendon graft 2 to the femur is performed. More specifically, as shown in FIG. 31, the other-end side bone plug 24 of the bone plug-attached tendon graft 2 is fixed inside the femur-side bone tunnel 9 formed at the portion where the tendon graft 2 is to be transplanted. This fixing operation is performed to fix the other-end side bone plug 24 of the bone plug-attached tendon graft 2 disposed inside the femur-side bone tunnel 9 at the step of disposing the collected tendon graft 2 at the portion to be reconstructed to the inside of the femur-side bone tunnel 9. The fixing method is carried out by screwing a fixing apparatus 97 such as a screw having a screw thread into the gap between the femur-side bone tunnel 9 and the other-end side bone plug 24. The method of fixing the other side of the tendon graft 2 to the femur is not limited to this method. For example, it is possible to adopt a method of mounting a fixing button having a diameter larger than the femur-side bone tunnel on the pulling member 26. It is also possible to adopt a method of striking a staple into the femur to fix the pulling member 26 thereto. If the bone plug (other-end side bone plug 24) is unnecessary in fixing the bone plug-attached tendon graft 2 to the femur, it is unnecessary to collect the other-end side bone plug 24 in collecting the tendon graft 2. In this case, the bone plug-attached tendon graft 2 has only the one-end side bone plug 21, with the femur side pulling member 26 sewed to an end of the tendon graft 2 at its femur side (other side). When the bone plug-attached tendon graft 2 has only the one-end side bone plug 21, it is possible to use bone plug-attached quadriceps femoris tendon or the like as the tendon graft.

The next step to be performed is the step of striking the fixing member 3 having the following construction into a portion disposed in the neighborhood of the one-end side opening in such a way that the main body part 32 of the fixing member 3 crosses the opening of the bone tunnel. The fixing member 3 has the main body part 32 provided with the through-hole 31 formed at the central portion thereof and the two spike parts 33, 34 which extend almost parallelly from both side edges of the main body part 32 with the spike parts 33, 34 spaced at the predetermined interval longer than the diameter of the one-end side bone tunnel and which can be stricken into the tibia. More specifically, the fixing member 3 having the following construction is stricken into the portion in the neighborhood of the tibia-side bone tunnel 8 in such a way that the main body part 32 of the fixing member 3 crosses the opening 81 of the tibia-side bone tunnel 8. The fixing member 3 has the main body part 32 provided with the through-hole 31 formed at the central portion thereof and the two spike parts 33, 34 which extend almost parallelly from both side edges of the main body part 32 with the spike parts 33, 34 spaced at the predetermined interval longer than the diameter of the tibia-side bone tunnel 8 and which can be stricken into the tibia 10.

Figure 32:
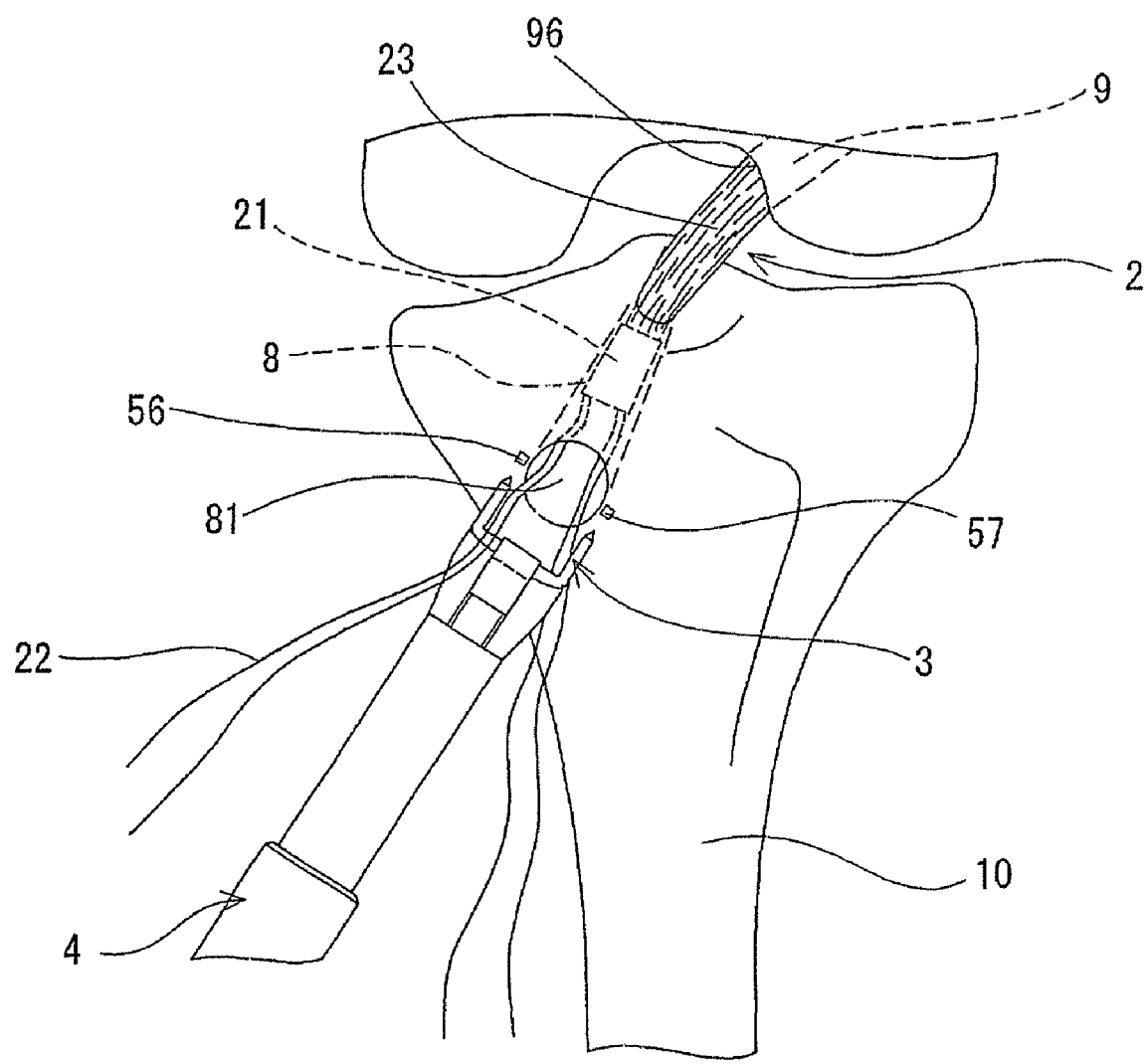
FIG. 32 is an explanatory view for explaining how a fixing member is stricken into a bone in the anterior cruciate ligament reconstruction method of the present invention.

More specifically, as shown in FIGS. 18 and 19, the striking tool 4 whose fixing member-gripping part 41 gripping the fixing member 3 is prepared. Thereafter as shown in FIG. 32, the proximal end portion 44b for being hammered (proximal-end surface) provided at the proximal end of the operation part 44 of the striking tool 4 gripping the fixing member 3 is hit with a hammer or the like to strike the fixing member (more specifically, the spike part 33, 34 of the fixing member 3) 3 into the pilot holes 56, 57. Thereafter the operation part 44 of the striking tool 4 is rotated reversely (rotated in the direction in which the operation part 44 is removed) to move the shaft part (and the fixing member-gripping part 41) 43 to the distal end of the cylindrical member 42 so that the fixing member 3 is released (removed) from the striking tool 4. Thereby it is possible to obtain a state where the main body part 32 of the fixing member 3 stricken into the portion disposed in the neighborhood of the open portion 81 of the tibia-side bone tunnel 8 crosses the open portion 81 (front opening) of the tibia-side bone tunnel 8. It is preferable that the pulling member 22 of the one-end side bone plug 21 of the bone plug-attached tendon graft 2 disposed inside the tibia-side bone tunnel 8 at the step of disposing the tendon graft 2 is extended from the open portion (front opening) 81 of the tibia-side bone tunnel 8 before striking the fixing member 3. More specifically, it is preferable to extend the pulling member 22 from the gap between the main body part 32 of the fixing member 3 gripped by the striking tool 4 and the open portion 81 (front opening) of the tibia-side bone tunnel 8. When the pilot hole is not formed, the fixing member 3 is directly stricken into the tibia 10 with the striking tool 4.

Figure 33:
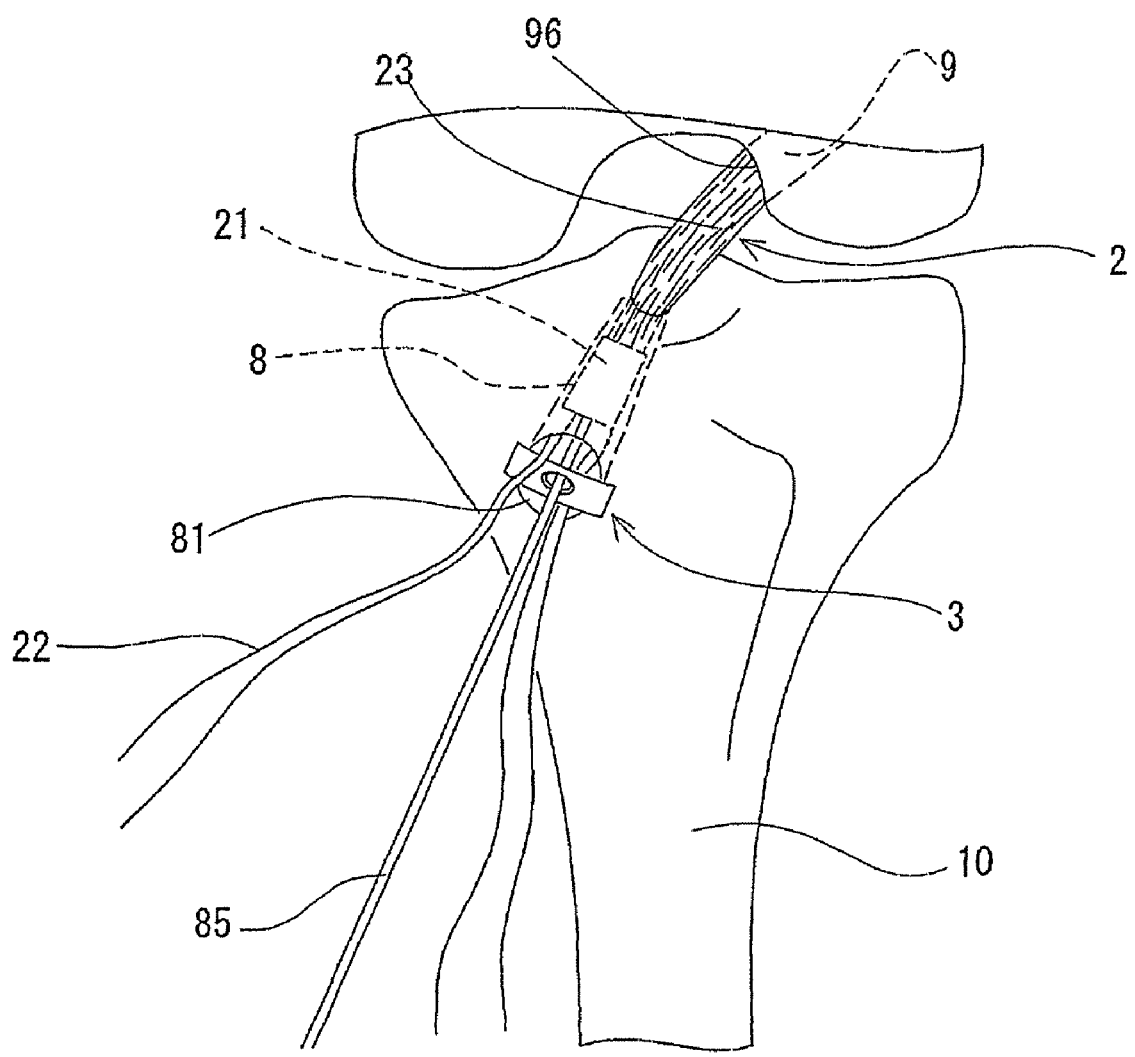
FIG. 33 is an explanatory view for explaining how a tensile force is adjusted in the anterior cruciate ligament reconstruction method of the present invention.

Thereafter the step of piercing a guide pin 85 to one of said bone plugs through the through-hole 31 of the fixing member 3 is performed. More specifically, as shown in FIG. 33, the guide pin 85 is pierced into the one-end side bone plug 21 disposed inside the tibia-side bone tunnel 8 at the step of disposing the tendon graft 2 at the portion to be reconstructed. It is preferable that the guide pin 85 is formed in the shape of a conic bar, a three-sided pyramidal bar or a four-sided pyramidal bar in its distal side so that the guide pin 85 can be pierced into the one-end side bone plug 21. Any type of the guide pin 85 can be used, provided that it can be pierced into the one-end side bone plug 21 and penetrated through the lumen 66 of the fixing screw 6 and brought into contact with the one-end side bone plug 21. It is preferable that a hole is formed in the one-end side bone plug 21 before the step of piercing the guide pin 85 into one of the bone plugs is performed. Thereby the step of piercing the guide pin 85 into one of the bone plugs can be easily performed.

The next step to be performed is the step of disposing the fixing screw 6 in such a way that the guide pin 85 penetrates through the lumen 66 of the fixing screw 6 and that the fixing screw 6 is advanced along the guide pin 85 to penetrate the guide pin 85 through-hole 31 of the fixing member 3 and bring the distal end of the fixing screw 6 into contact with the bone plug. The fixing screw 6 includes the shaft part 65 having the self-tap portion 63 and the male screw portion 62 both of which can be penetrated through the through-hole 31 of the fixing member 3 and is screwed into the bone plug; the head part 61 which is disposed at the proximal end of the shaft part 65 and can be brought into contact with the main body part 32 on the peripheral edge of the through-hole 31 of the fixing member 3; and the lumen 66 which is extended from the proximal end of the head part 61 to the distal end of the shaft part 65 and through which the guide pin 85 can be penetrated.

Thereby it is possible to obtain a state where the guide pin 85 penetrates through the lumen 66 of the fixing screw 6. Thereafter the fixing screw 6 is advanced toward the distal end of the guide pin 85. As a result, the distal end (the self-tap portion 63) of the fixing screw 6 contacts the one-end side bone plug 21 after the fixing screw 6 penetrates through the through-hole 31 of the fixing member 3. Thereby the fixing screw 6 can be securely screwed into the one-end side bone plug 21 at a position and an angle at which the guide pin 85 has been pierced into the one-end side bone plug 21.

Figure 34:
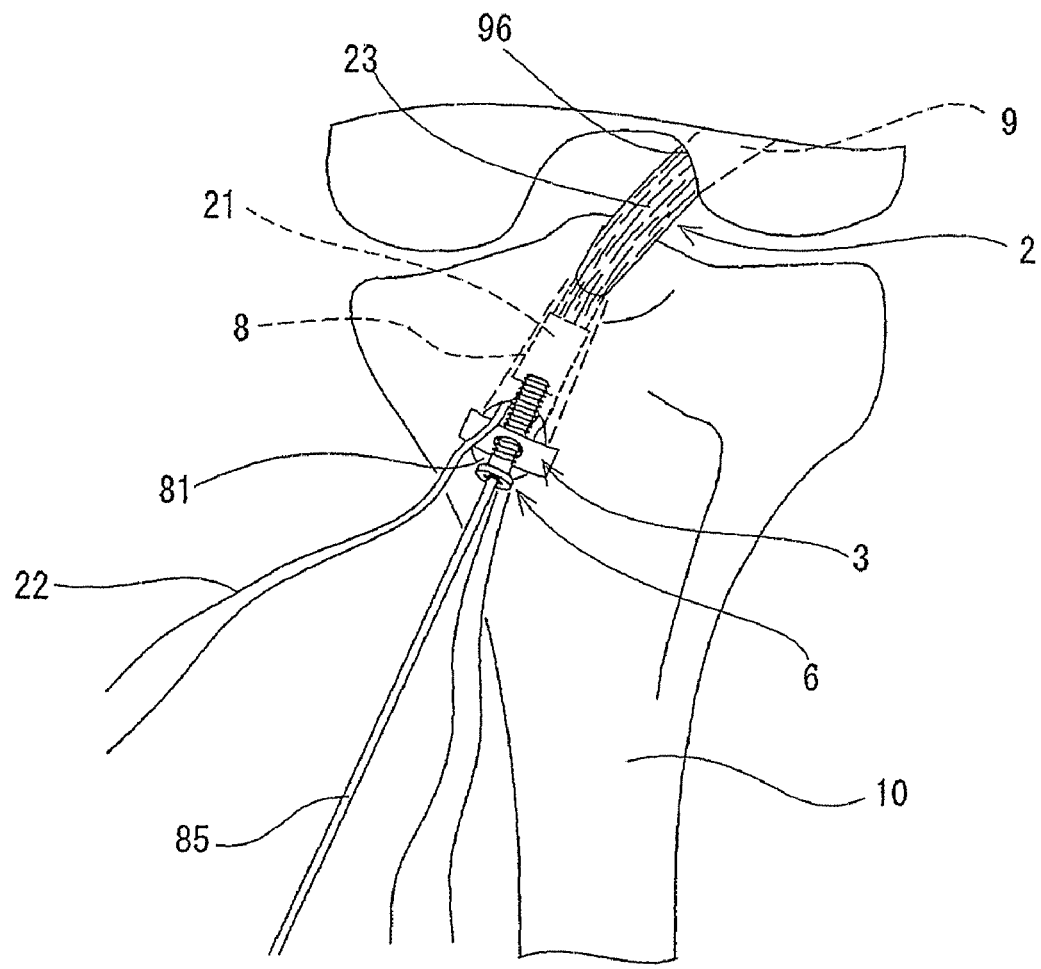
FIG. 34 is an explanatory view for explaining how the tensile force is adjusted in the anterior cruciate ligament reconstruction method of the present invention.

Thereafter the step of screwing the fixing screw 6 into the bone plug 21 is performed. More specifically, as shown in FIG. 34, the fixing screw 6 which has penetrated through the through-hole 31 of the fixing member 3 is screwed into the one-end side bone plug 21 to some extent before the pulling member 22 is pulled. In other words, before the bone plug-attached tendon graft 2 obtains a tensile force, the fixing screw 6 which has been penetrated into the through-hole 31 of the fixing member 3 is screwed through the one-end side bone plug 21 to some extent. The fixing screw 6 is screwed into the one-end side bone plug 21 by using a screwing appliance 101, shown in FIGS. 26 through 28, which is hollow from its distal end to its proximal end. The proximal side of the guide pin 85 is inserted into the screwing appliance 101 from a distal-end opening 103 thereof. Thereafter the screwing appliance 101 is advanced to engage a distal portion 102 with the engaging groove 64 of the fixing screw 6. By rotating (rotating the fixing screw 6 in a tightening direction) the screwing appliance 101, the fixing screw 6 rotates in the tightening direction. The self-tap portion 63 of the fixing screw 6 penetrates into the one-end side bone plug 21 of the bone plug-attached tendon graft 2 with the self-tap portion 63 cutting the one-end side bone plug 21. If the one-end side bone plug 21 rotates together with the rotation of the screwing appliance 101, it is preferable to fix the one-end side bone plug 21 with a clamp or the like.

Figure 35:
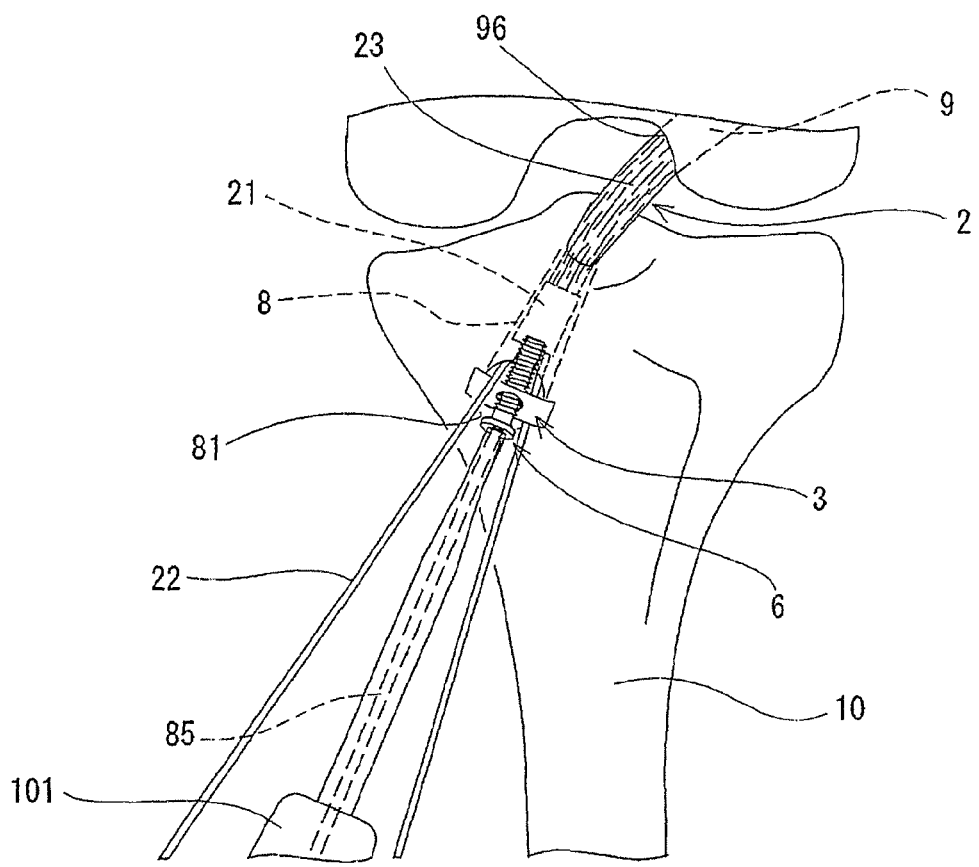
FIG. 35 is an explanatory view for explaining how the tensile force is adjusted in the anterior cruciate ligament reconstruction method of the present invention.

The next step to be performed is the step of pulling the pulling member 22 mounted on the bone plug 21 and extended from the gap between the main body part 32 of the fixing member 3 and the opening of the bone tunnel and measuring a pulling-caused tensile force applied to the pulling member 22. More specifically, as shown in FIG. 35, the pulling member 22 extended from the gap between the main body part 32 of the fixing member 3 and the opening (front opening) 81 of the tibia-side bone tunnel 8 is pulled in a direction in which the pulling member 22 recedes from the other-end side bone plug (fixing appliance at femur side) 24. Thereby the bone plug-attached tendon graft 2 (more specifically, tendon 23) obtains the tensile force caused by the pulling performed between the one-end side bone plug 21 of the bone plug-attached tendon graft 2 and the other-end side bone plug (or fixing appliance at femur side) 24 thereof. Thereafter a pulling force (pulling force before the head part 61 of the fixing screw 6 contacts the main body part 32 of the fixing member 3) of the pulling member 22 caused by the pulling of the pulling member 22 is found by using a pulling apparatus or a force gauge (not shown) or the like. In this embodiment, the pulling member 22 is pulled at a force of 60 N. It is desirable to keep the pulling member 22 pulled for a few minutes. Thereby it is possible to obtain a sufficient load relaxation and prevent the tensile force of the tendon graft from decreasing owing to creep deformation that occurs among the femur, the bone plug-attached tendon graft, and the tibia, after the fixing of the bone plug-attached tendon graft to the bone tunnel finishes. In pulling the pulling member 22, the pulling apparatus or the force gauge not shown is used to measure the pulling force of the pulling member 22.

Figure 36:
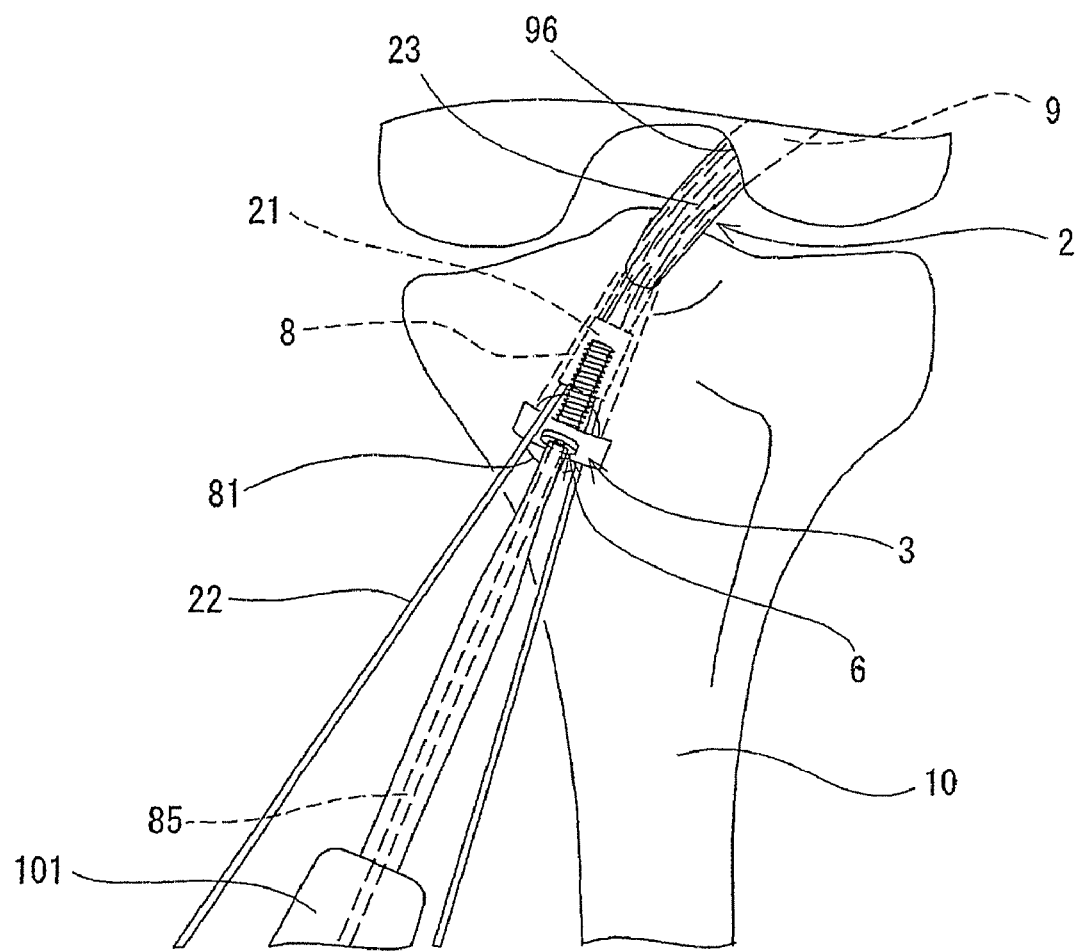
FIG. 36 is an explanatory view for explaining how the tensile force is adjusted in the anterior cruciate ligament reconstruction method of the present invention.

The next step to be performed is the step of progressing screwing of the fixing screw 6 into the bone plug and bringing the head part 61 of the fixing screw 6 into contact with the fixing member 3. More specifically, as shown in FIG. 36, with the pulling member 22 extended from the gap between the main body part 32 of the fixing member 3 and the opening (front opening) 81 of the tibia-side bone tunnel 8 kept pulled, the fixing screw 6 that has passed through the through-hole 31 of the fixing member 3 and the opening (front opening) 81 of the tibia-side bone tunnel 8 is screwed into the one-end side bone plug 21 to engage the fixing screw 6 (male screw portion 62 of the fixing screw 6) with the female screw portion formed on the one-end side bone plug 21. The fixing screw 6 is screwed into the one-end side bone plug 21 by using the screwing appliance 101, shown in FIGS. 26 through 28, which is hollow from its distal end to its proximal end. More specifically, after the proximal side of the guide pin 85 is inserted into the hollow screwing appliance 101 from the distal-end opening 103 thereof, the screwing appliance 101 is advanced to engage the distal end 102 thereof with the engaging groove 64 of the fixing screw 6 and rotate the fixing screw 6 (rotated in the direction in which it is tightened). In this case, the one-end side bone plug 21 is pulled by the pulling member 22 in the direction in which the pulling member 22 recedes from the other-end side bone plug (or the fixing appliance at the femur side) 24. Thus the one-end side bone plug 21 is restrained from rotating together with the rotation of the screwing appliance 101. If the one-end side bone plug 21 rotates together with the rotation of the screwing appliance 101, it is preferable to fix the one-end side bone plug 21 with a clamp or the like. The rotation of the fixing screw (screwing appliance 101) 6 is continued until the head part 61 of the fixing screw 6 contacts the main body part 32 of the fixing member 3.

The next step to be performed is the tensile force-adjusting step of adjusting the tensile force applied to the tendon graft by progressing the screwing of the fixing screw 6 into the one-end side bone plug 21 till the tensile force applied to the pulling member 22 being measured attains a predetermined value after the contact of the head part 61 of the fixing screw 6 with the main body part 32 of the fixing member 3.

The pulling force of the pulling member 22 decreases each time the fixing screw 6 is rotated (the fixing screw 6 is rotated in the direction in which it is tightened), after the head part 61 of the fixing screw 6 contacts the main body part 32 of the fixing member 3. In this case, a decreased amount of the pulling force is born by the fixing screw 6. The pulling force of the pulling member 22 increases each time the fixing screw 6 is reversely rotated (the fixing screw 6 is rotated in the direction in which it is removed) after the head part 61 of the fixing screw 6 contacts the main body part 32 of the fixing member 3. In this case, the pulling force which has been born by the fixing screw 6 decreases by an increased amount of the pulling force.

Thus is utilized to adjust the tensile force applied to the tendon graft. That is, by adjusting the amount of the screwing of the fixing screw 6 into the one-end side bone plug 21 till the tensile force applied to the pulling member being measured decreases to a predetermined value after the contact of the head part 61 of the fixing screw 6 with the main body part 32 of the fixing member 3. More specifically, by using the pulling apparatus or the force gauge (not shown), it is possible to set the initial tensile force applied to the bone plug-attached tendon graft by finding a pulling force before the head part 61 of the fixing screw 6 contacts the main body part 32 of the fixing member 3 and a decrease amount of the pulling force of the pulling member 22 when the rotation of the fixing screw 6 is stopped with the head part 61 of the fixing screw 6 in contact with the main body part 32 of the fixing member 3.

For example, the tensile force-adjusting step is performed by progressing the screwing of the fixing screw 6 into the one-end side bone plug 21 till the tensile force becomes 20 N by using the pulling apparatus or the force gauge (not shown) while the tensile force is being checked after the head part 61 contacts the main body part 32. The bone plug-attached tendon graft 2 is fixed at a tensile force before the head part 61 of the fixing screw 6 contacts the main body part 32 of the fixing member 3 and a tensile force equivalent to a decrease amount (change amount) of the pulling force of the pulling member 22 when the rotation of the fixing screw 6 is stopped after the head part 61 of the fixing screw 6 contacts the main body part 32 of the fixing member 3. In this embodiment, the bone plug-attached tendon graft 2 is fixed with the pulling force of 40 N being born by the fixing screw 6. In other words, the initial tensile force of the bone plug-attached tendon graft 2 is 40 N.

At this time, when the initial tensile force of the bone plug-attached tendon graft 2 is smaller than a tensile force intended by the operator, the fixing screw 6 is further rotated (the fixing screw 6 is rotated in the direction in which it is tightened) to increase the pulling force born by the fixing screw 6. Thereby the tensile force intended by the operator is obtained. When the initial tensile force of the bone plug-attached tendon graft 2 is larger than the tensile force intended by the operator, the fixing screw 6 is rotated reversely (the fixing screw 6 is rotated in the direction in which it is removed) to decrease the pulling force born by the fixing screw 6. Thereby the tensile force intended by the operator is obtained.

Figure 37:
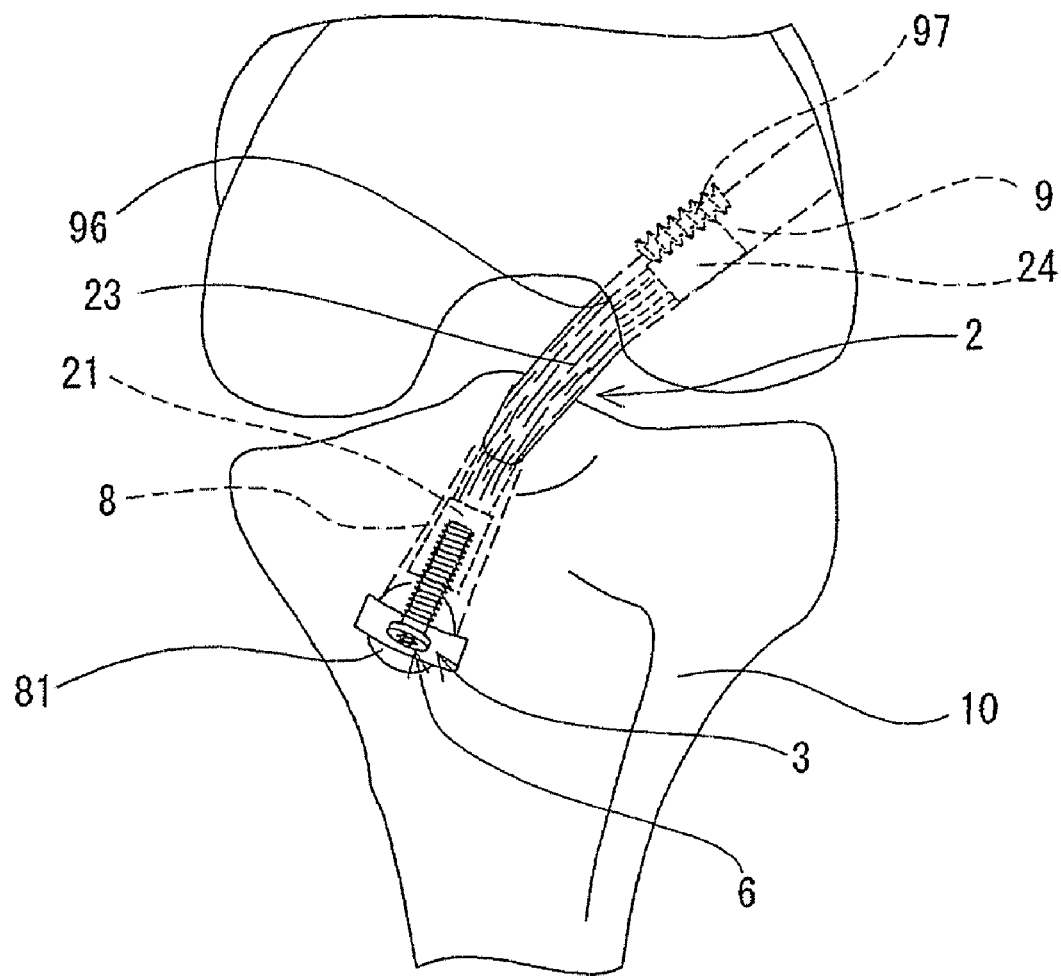
FIG. 37 is an explanatory view for explaining how the tensile force is adjusted in the anterior cruciate ligament reconstruction method of the present invention.

This method allows the tensile force of the bone plug-attached tendon graft 2 to be securely fixed at the tensile force intended by the operator. The guide pin and the pulling apparatus or the force gauge (not shown) are removed to release the state in which the pulling member 22 is pulled. Thereby the state shown in FIG. 37 is obtained. That is, the method of the present invention of reconstructing the anterior cruciate ligament finishes by using the bone plug-attached tendon graft to be transplanted.

The pulling member 22 of this embodiment does not play a part in fixing the one-end side bone plug 21 of the bone plug-attached tendon graft 2 to the tibia-side bone tunnel. In other words, the one-end side bone plug 21 can be directly fixed to the tibia-side bone tunnel by means of the fixing screw 6. Thereby it is possible to decrease deviation of the fixing position of the one-end side bone plug 21 to a smaller extent than the case in which the one-end side bone plug 21 is fixed by inserting the fixing screw for fixing the tendon graft or the expandable fixing apparatus for fixing the tendon graft between the tibia-side bone tunnel 8 and the tibia-side bone plug 21. That is, the fixing tool 1 is capable of fixing the one-end side bone plug 21 at the initial tensile force intended by the operator.

In the tensile force-adjustable fixing tool of the present invention for fixing the bone plug-attached tendon graft to be transplanted and the anterior cruciate ligament reconstruction method to be carried out by using the bone plug-attached tendon graft, it is possible to fix the bone plug-attached tendon graft to the bone tunnel at the initial tensile force intended by the operator. More specifically, it is possible to fix the bone plug-attached tendon graft at the initial tensile force intended by the operator by finding the pulling force before the head part of the fixing screw contacts the main body part of the fixing member and the decrease amount of the pulling force of the pulling member when the rotation of the fixing screw is stopped with the head part of the fixing screw in contact with the main body part of the fixing member.

What is claimed is:

1. An anterior cruciate ligament reconstruction method performed using a tendon graft comprised of first and second bone plugs each attached to a respective end of a tendon, each of the first and second bone plugs being made of a piece of bone, and each of the first and second bone plugs having an attached pulling member, the method comprising:

forming a femur-side bone tunnel in a femur and a tibia-side bone tunnel in a tibia, the tibia-side bone tunnel possessing an opening which opens to outside the tibia;

disposing the first bone plugs inside the tibia-side bone tunnel and the second bone plug inside the femur-side bone tunnel;

striking a fixing member while the fixing member is positioned so that a main body of the fixing member crosses the opening of the tibia-side tunnel, the fixing member also having a through-hole passing through the main body and two spike parts extending away from the main body part and spaced apart from one another by a distance greater than a diameter of the opening of the tibia-side bone tunnel, the striking of the fixing member causing the spike parts to penetrate the tibia;

inserting a guide pin through the through-hole of the fixing member so the guide pin extends towards the first bone plug in the tibia-side bone tunnel, the guide pin being inserted through the through-hole after the spike parts penetrate the tibia as a result of the striking of the fixing member;

moving a fixing screw toward the first bone plug in the tibia-side bone tunnel, the fixing screw having a shaft part with a self-tap portion and a male screw portion, the fixing screw also having a head part at a rear end of the shaft part and a lumen extending from a rear end of the head part to a front end of the shaft part, the moving of the fixing screw toward the first bone plug in the tibia-side bone tunnel including moving the fixing screw while the guide pin is in the lumen of the fixing screw so that the fixing screw is guided by the guide pin toward the first bone plug in the tibia-side bone tunnel, the moving of the fixing screw toward the first bone plug in the tibia-side bone tunnel also including moving the fixing screw so that the fixing screw passes through the through-hole of the fixing member and the front end of the shaft part of the fixing screw contacts the first bone plug in the tibia-side bone tunnel, the moving of the fixing screw occurring after the inserting of the guide pin;

screwing the fixing screw into the piece of bone forming the first bone plug in the tibia-side bone tunnel;

pulling the pulling member mounted on the first bone plug and measuring a pulling-caused tensile force applied to the pulling member mounted on the first bone plug;

progressing screwing of the fixing screw into the piece of bone forming the first bone plug in the tibia-side bone tunnel to move the head part of the fixing screw into contact with the fixing member; and adjusting the tensile force applied to the pulling member mounted on said first bone plug by progressing screwing of the fixing screw into the piece of bone forming the first bone plug until the tensile force applied to the pulling member mounted on said first bone plug attains a predetermined value after the head part of the fixing screw contacts the fixing member.

2. An anterior cruciate ligament reconstruction method according to claim 1, further comprising forming pilot holes in the tibia adjacent the opening of the tibia-side bone tunnel, each of the two spike parts of the fixing member being positioned in a respective one of the pilot holes during the striking of the fixing member, the forming of the pilot holes occurring before the striking of the fixing member.

3. An anterior cruciate ligament reconstruction method comprising:

preparing a tendon graft comprised of a tendon having opposite ends and a first bone plug attached to one end of the tendon and a second bone plug attached to an opposite end of the tendon, the first and second bone plugs each being made of a piece of bone;

mounting a pulling member on the first bone plug and the second bone plug;

forming a femur-side bone tunnel in a femur and a tibia-side bone tunnel in a tibia, the tibia-side bone tunnel possessing an opening which opens to outside the tibia;

disposing the first bone plug inside the tibia-side bone tunnel and the second bone plug inside the femur-side bone tunnel;

striking a fixing member while the fixing member is positioned so that a main body of the fixing member crosses the opening of the tibia-side tunnel, the fixing member also having a through-hole passing through the main body and two spike parts extending away from the main body part and spaced apart from one another by a distance greater than a diameter of the opening of the tibia-side bone tunnel, the striking of the fixing member causing the spike parts to penetrate the tibia;

positioning a guide pin so that the guide pin passes through the through-hole of the fixing member and extends towards the first bone plug in the tibia-side bone tunnel;

moving a fixing screw toward the first bone plug in the tibia-side bone tunnel, the fixing screw having a shaft part with a self-tap portion and a male screw portion, the fixing screw also having a head part at a rear end of the shaft part and a lumen extending from a rear end of the head part to a front end of the shaft part, the moving of the fixing screw toward the first bone plug in the tibia-side bone tunnel including moving the fixing screw while the guide pin is in the lumen of the fixing screw so that the fixing screw is guided by the guide pin toward the first bone plug in the tibia-side bone tunnel, the moving of the fixing screw toward the first bone plug in the tibia-side bone tunnel also including moving the fixing screw so that the fixing screw passes through the through-hole of the fixing member and the front end of the shaft part of the fixing screw contacts the first bone plug in the tibia-side bone tunnel;

screwing the fixing screw into the piece of bone forming the first bone plug in the tibia-side bone tunnel;

pulling the pulling member mounted on the first bone plug in the tibia-side bone tunnel and measuring a pulling-caused tensile force applied to the pulling member mounted on the first bone plug;

progressing screwing of the fixing screw into the piece of bone forming the first bone plug in the tibia-side bone tunnel to move the head part of the fixing screw into contact with the fixing member; and adjusting the tensile force applied to the pulling member mounted on said first bone plug by progressing screwing of the fixing screw into the piece of bone forming the first bone plug until the tensile force applied to the pulling member mounted on said first bone plug attains a predetermined value after the head part of the fixing screw contacts the fixing member.

4. The anterior cruciate ligament reconstruction method according to claim 3, further comprising forming pilot holes in the tibia adjacent the opening of the tibia-side bone tunnel, each of the two spike parts of the fixing member being positioned in a respective one of the pilot holes during the striking of the fixing member, the forming of the pilot holes occurring before the striking of the fixing member.

5. An anterior cruciate ligament reconstruction method comprising:

preparing a tendon graft in which a piece of bone constituting a first bone plug is attached to one end of a tendon and another piece of bone constituting a second bone plug is attached to an end of the tendon, the tendon graft possessing one end at which the first bone plug is located and an opposite end at which the second bone plug is located mounting a pulling member on each of said first and second bone plugs of said tendon graft respectively;

forming a femur-side bone tunnel and a tibia-side bone tunnel on a portion to be reconstructed;

disposing said tendon graft at said portion to be reconstructed in such a way that the first bone plug is positioned inside said tibia-side bone tunnel and the second bone plug is positioned inside said femur-side bone tunnel;

fixing said opposite end of said tendon graft relative to said femur-side bone tunnel;

striking a fixing member, the fixing member having a main body part provided with a through-hole formed at a central portion thereof and two spike parts which extend almost parallel to each other and extending from both side edges of said main body part with said spike parts spaced at a distance greater than a diameter of an opening of said tibia-side bone tunnel, the striking of the fixing member occurring when the fixing member is positioned such that said main body part crosses the opening of said tibia-side bone tunnel and said spike parts are in a neighborhood of the tibia-side bone tunnel;

positioning a guide pin so the guide pin passes through said through-hole of said fixing member and extends toward the first bone plug in the tibia-side bone tunnel;

disposing a fixing screw including a shaft part having a self-tap portion and a male screw portion both configured to pass through said through-hole of said fixing member and to be screwed into said first bone plug, a head part disposed at a rear end of said shaft part to contact said main body part on a peripheral edge of said through-hole of said fixing member, and a lumen extending from a rear end of said head part to a front end of said shaft part, the disposing of said fixing screw including advancing said fixing screw along said guide pin while said guide pin is positioned in said lumen of said fixing screw so said fixing screw passes through said through-hole of said fixing member and a front end of said fixing screw contacts said first bone plug;

screwing said fixing screw into said piece of bone constituting said first bone plug;

pulling said pulling member mounted on said first bone plug and extending through a gap between said main body part of said fixing member and the opening of said tibia-side bone tunnel, and measuring a pulling-caused tensile force applied to said pulling member mounted on said first bone plug;

progressing screwing of said fixing screw into said piece of bone constituting said first bone plug to bring said head part of said fixing screw into contact with said fixing member; and adjusting said tensile force applied to said pulling member mounted on said first bone plug by progressing screwing of said fixing screw into said piece of bone constituting said first bone plug until said tensile force applied to said pulling member mounted on said first bone plug being measured attains a predetermined value after said head part of said fixing screw contacts said fixing member.

6. The anterior cruciate ligament reconstruction method according to claim 5, further comprising forming pilot holes adjacent the opening of the tibia-side bone tunnel, each of said two spike parts of said fixing member being positioned in a respective one of said pilot holes during said striking of said fixing member, the forming of the pilot holes occurring before said striking of said fixing member.

* * * * *